(12) United States Patent
Asirvatham et al.

(10) Patent No.: US 12,114,984 B2
(45) Date of Patent: Oct. 15, 2024

(54) SYSTEM AND APPARATUS FOR GENERATING IMAGING INFORMATION BASED ON AT LEAST A SIGNAL

(71) Applicant: Anumana, Inc., Cambridge, MA (US)

(72) Inventors: Samuel J. Asirvatham, Rochester, MN (US); Murali Aravamudan, Andover, MA (US); Ajit Rajasekharan, West Windsor, NJ (US)

(*) Notice: Subject to any disclaimer, the term of this patent is extended or adjusted under 35 U.S.C. 154(b) by 0 days.

(21) Appl. No.: 18/517,640

(22) Filed: Nov. 22, 2023

(65) Prior Publication Data

US 2024/0164688 A1 May 23, 2024

Related U.S. Application Data

(60) Provisional application No. 63/506,652, filed on Jun. 7, 2023, provisional application No. 63/427,404, filed on Nov. 22, 2022.

(51) Int. Cl.
*A61B 5/00* (2006.01)
*A61B 5/327* (2021.01)
*G06N 3/08* (2023.01)

(52) U.S. Cl.
CPC .............. *A61B 5/327* (2021.01); *G06N 3/08* (2013.01)

(58) Field of Classification Search
None
See application file for complete search history.

(56) References Cited

U.S. PATENT DOCUMENTS 11,445,918 B2   9/2022 Peterson
2019/0223819 A1  7/2019 Mansi et al.
(Continued)

FOREIGN PATENT DOCUMENTS

| CN | 113171106 A | 7/2021 |
| EP | 4085838 A1 | 11/2022 |
| WO | 2022231988 A1 | 11/2022 |

OTHER PUBLICATIONS

Skandarani et al. "Generative Adversarial Networks in Cardiology" Canadian Journal of Cardiology 38 (2022) 196-203 https://www.sciencedirect.com/science/article/pii/S0828282X210086 (Year: 2021).*

(Continued)

*Primary Examiner* — Shirley X Jian
(74) *Attorney, Agent, or Firm* — Caldwell Intellectual Property Law

(57) ABSTRACT

A system for generating imaging information based on at least a signal includes at least a processor and a memory communicatively connected thereto, where the memory contains instructions configuring the at least a processor to receive a plurality of unconditioned electrocardiogram images, a plurality of conditioned electrocardiogram images and a corpus of ECG signals. Additionally, the processor learns at least a discrepancy between the plurality of unconditioned electrocardiogram images and the plurality of conditioned electrocardiogram images using a self-supervised machine learning model. Further, the processor generates a generative model as a function of the at least a discrepancy wherein generating the generative model comprises training the generative model using generative training data wherein the generative training data correlates at least an ECG signal from the corpus of ECG signals input to an output echocardiogram datum and output a diagnosis as a function of the output echocardiogram datum.

20 Claims, 20 Drawing Sheets

(56) References Cited

U.S. PATENT DOCUMENTS

| | | |
|---|---|---|
| 2021/0287442 A1* | 9/2021 | Ramachandra Iyer ..................... G06F 3/017 |
| 2022/0000410 A1 | 1/2022 | Baram |
| 2022/0189634 A1 | 6/2022 | Wagner et al. |
| 2022/0218289 A1 | 7/2022 | Attia et al. |
| 2022/0249031 A1 | 8/2022 | Clifton et al. |
| 2023/0028783 A1* | 1/2023 | Zimmerman .......... A61B 5/361 |

OTHER PUBLICATIONS

Zhu et al. "Electrocardiogram generation with a bidirectional LSTM-CNN generative adversarial network" Scientific Reports 2019 https://pubmed.ncbi.nlm.nih.gov/31043666/ (Year: 2019).*

"Autoregressive generative adversarial networks" Workshop track—ICLR 2018 https://openreview.net/pdf?id=Hyo9zDuIz (Year: 2018).*

¢ Zhu et al. âElectrocardiogram generation with a bidirectional LSTM-CNN generative adversarial networkâ Scientific Reports 2019 (Year: 2019).*

ÂAutoregressive generative adversarial networksâ Workshop track—ICLR 2018 (Year: 2018).*

Naz et al., From ECG signals to images: a transformation based approach for deep learning, (journal), Feb. 10, 2021, PeerJ Computer Science, 7: e386, National Library of Medicine.

* cited by examiner

SYSTEM AND APPARATUS FOR GENERATING IMAGING INFORMATION BASED ON AT LEAST A SIGNAL

CROSS-REFERENCE TO RELATED APPLICATIONS

This application claims the benefit of priority of U.S. Provisional Application Ser. No. 63/427,404, filed on Nov. 22, 2022, and entitled "SYSTEM AND METHOD FOR GENERATING ECHOCARDIOGRAM INFORMATION FROM ELECTROCARDIOGRAM" and U.S. Provisional Application Ser. No. 63/506,652, filed Jun. 7, 2023, and entitled "SYSTEM AND METHOD FOR GENERATING ECHOCARDIOGRAM INFORMATION FROM ELECTROCARDIOGRAM" which are incorporated by reference herein in their entirety.

FIELD OF THE INVENTION

The present invention generally relates to the field of medical technology. In particular, the present invention is directed to generating imaging information from at least a signal.

BACKGROUND

Echocardiograms have conventionally been essential for diagnosing various heart diseases, including congenital heart disease, cardiomyopathy, infective endocarditis, and aortic aneurysm. However, compared to electrocardiograms (ECG), echocardiograms (ECHO) are not performed as frequently, primarily because of their higher cost.

SUMMARY OF THE DISCLOSURE

In an aspect, a system for generating imaging information based on at least a signal includes at least a processor and a memory communicatively connected to the at least a processor where the memory contains instructions configuring the at least a processor to receive a plurality of unconditioned electrocardiogram images, a plurality of conditioned electrocardiogram images and a corpus of ECG signals. Further, the processor generates a generative model as a function of the plurality of ECG images and the ECG data repository wherein generating the generative model includes training the generative model using generative training data and output echocardiogram data as a function of the trained generative model at a viewer.

In another aspect a method for generating imaging information based on at least a signal includes receiving, by at least a processor, a plurality of unconditioned electrocardiogram images. Additionally, receiving, by the at least a processor, a plurality of conditioned electrocardiogram images and receiving, by the at least a processor, a corpus of ECG signals. Further, the processor generates a generative model as a function of the plurality of ECG images and the ECG data repository wherein generating the generative model includes training the generative model using generative training data and output echocardiogram data as a function of the trained generative model at a viewer.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating imaging information based on at least a signal. In an embodiment, the method includes receiving, by at least a processor, a plurality of unconditioned electrocardiogram images. Additionally, receiving, by the at least a processor, a plurality of conditioned electrocardiogram images and receiving, by the at least a processor, a corpus of ECG signals. Additionally, the processor learns at least a discrepancy between the plurality of unconditioned electrocardiogram images and the plurality of conditioned electrocardiogram images using a self-supervised machine learning model. Further, the processor generates a generative model as a function of the at least a discrepancy wherein generating the generative model comprises training the generative model using generative training data wherein the generative training data correlates at least an ECG signal from the corpus of ECG signals input to an output echocardiogram datum and output a diagnosis as a function of the output echocardiogram datum.

Aspects of the present disclosure can be used to understand differentiating aspects of conditioned and unconditioned electrocardiogram images. Aspects of the present disclosure can also be used to help surgeons output an accurate diagnosis. This is so, at least in part, because the generative model uses at least an ECG signal from the corpus of ECG signals to output echocardiogram datum.

Figure 1:
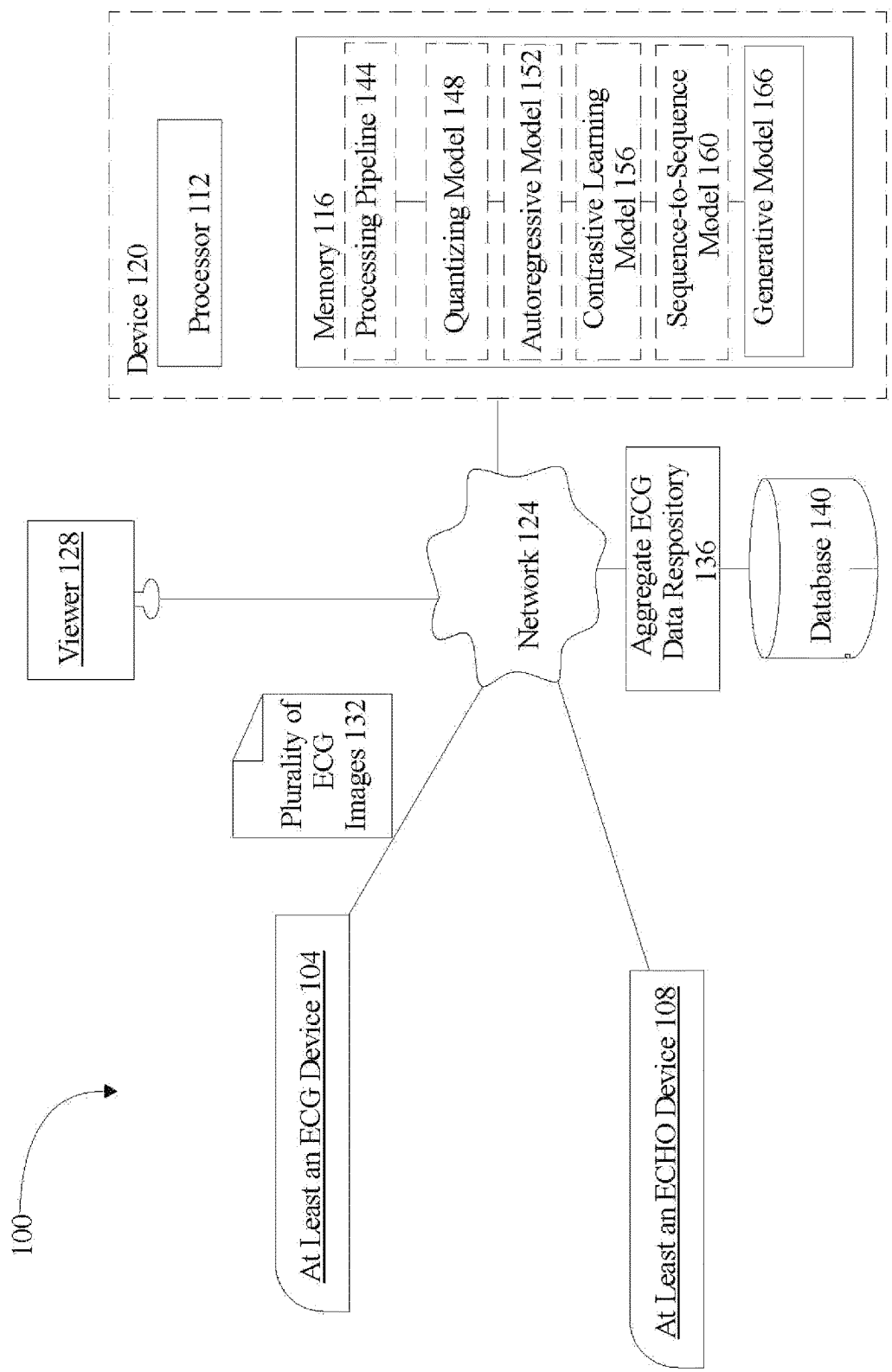
FIG. 1 is a flow diagram illustrating a system for generating imaging information based on at least a signal.

Referring now to FIG. 1, an exemplary embodiment of a system for generating imaging information based on at least a signal is illustrated. System 100 includes at least an electrocardiogram (ECG) device 104. As used herein, "an electrocardiogram device" refers to medical instrument used to record the electrical activity of the heart over a period of time. In a non-limiting embodiment, an ECG device may comprise electrodes, lead wires, an ECG machine and the like. Electrodes may comprise small, adhesive pads that are attached to a patient's skin at specific locations on the chest, arms, and legs. The electrodes may detect electrical impulses produced by the heart. Lead wires may be used to connect electrodes to the ECG machine. The ECG machine may be the main unit that receives the electrical signals from the electrodes. The ECG machine may amplify the signal and convert them into a visual representation, such as a waveform. System 100 includes at least an echocardiogram (ECHO) device 108. As used herein, an "ECHO device" refers to a medical instrument used to perform an echocardiography which is a diagnostic test that uses ultrasound waves to create images of a heart. An ECHO device may comprise a transducer, computer console, display monitor and the like. The transducer may be a small, handheld device that emits high-frequency sound waves (ultrasound) when placed on the patient's chest. The computer console may process the echoes to create live images of the heart which are then displayed on a monitor attached to the console. In non-limiting embodiments, at least an ECHO device may include a transthoracic echocardiogram (TTE), transesophageal echocardiogram (TEE), stress echocardiogram, doppler echocardiogram, and the like. A TEE functions by moving the transducer outside the chest wall to view the heart. The TEE functions by inserting a transducer down the esophagus of the patient to obtain a closer view of certain parts of the heart. A Stress echocardiogram is conducted during or immediately after exercising to assess how the heart functions under stress. The Doppler Echocardiogram measure the speed and direction of blood flow within the heart.

System includes a processor 112. Computing devices include a processor 112 communicatively connected to a memory 116. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, processor 112 may include any computing device as described in this disclosure, such as device 120, including without limitation a microcontroller, microprocessor, digital signal processor (DSP) and/or system on a chip (SoC) as described in this disclosure. Processor 112 may include, be included in, and/or communicate with a mobile device such as a mobile telephone or smartphone. Processor 112 may include a single computing device operating independently, or may include two or more computing device operating in concert, in parallel, sequentially or the like; two or more computing devices may be included together in a single computing device or in two or more computing devices. Processor 112 may interface or communicate with one or more additional devices as described below in further detail via a network interface device, such as network 124. Network interface device may be utilized for connecting Processor 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 112 may include but is not limited to, for example, a computing device or cluster of computing devices in a first location and a second computing device or cluster of computing devices in a second location. Processor 112 may include one or more computing devices dedicated to data storage, security, distribution of traffic for load balancing, and the like. Processor 112 may distribute one or more computing tasks as described below across a plurality of computing devices of computing device, which may operate in parallel, in series, redundantly, or in any other manner used for distribution of tasks or memory between computing devices. Processor 112 may be implemented, as a non-limiting example, using a "shared nothing" architecture.

With continued reference to FIG. 1, processor 112 may be designed and/or configured to perform any method, method step, or sequence of method steps in any embodiment described in this disclosure, in any order and with any degree of repetition. For instance, processor 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

System 100 also comprises Viewer 128. Viewer 128 generally includes LCD, CRT monitors, or the like. In some embodiments, viewer 128 may further include a user interface or a web browser through which a user can interact with an implementation of the subject matter described herein. For example, the user may input description of the input, structured data of knowledge about the input serialized into sentences, or any other data into the system. Although viewer 128 may be depicted as being directly coupled to processor 112, it is to be understood that a variety of other arrangements are possible. For example, viewer 128 may be directly to ECG or ECHO device, or the like.

With continued reference to FIG. 1, processor 112 is configured to receive a plurality of electrocardiogram images 132. An electrocardiogram is a measurement of the electrical activity of a mammal's heart. The pumping action of the heart is driven by the continuous cycle of electrical polarization and de-polarization of the heart muscle. This electrical activity can be captured by an electrocardiogram, whereby electrodes are placed on the surface of a subject (e.g., on the subject's chest and limbs) and the electrical potential is measured over a period of time between pairs of electrodes. The electrical signal captured by this process forms an electrocardiogram. When the electrocardiogram is plotted to show the variance in electrical potential between electrodes over time, a waveform or ECG tracing can be seen that shows the heart's polarization and de-polarization in each of one or more cardiac cycles. For the purposes of this specification, an electrocardiogram may include the traditional 12 leads, additional leads, or any number of leads to as few as a single lead. Additionally, the ECG may be acquired from adhesive electrodes, conductive electrodes, capacitive electrodes, handheld electrodes, worn/garment electrodes, subcutaneous electrodes, electrodes affixed to implanted devices or any combination thereof. As used herein an "ECG image" is a representation of the electrical activity of the heart over a period of time. In non-limiting embodiments, an ECG image may include a 2D and/or 3D representation of electrical activity of a heart, samples of electrical activity of the heart and/or samples usable to reconstruct a 2D and/or 3D representation of the electrical activity of the heart, graphic representations, waveforms, intervals, or the like.

With reference to FIG. 1, processor 112 is configured to receive an aggregate ECG data repository 136. As used herein an "aggregate ECG data repository" is a repository of data that can be obtained from an ECG that pertains to information that is typically obtained from an echocardiogram. In non-limiting embodiments, ECG data may comprise a corpus of ECG signals. As used herein, a "corpus of ECG signals" refers to a comprehensive collection or database of ECG signal data, such as database 140. In some embodiments, an ECG signal may comprise at least data interpreting P waves, QRS complexes, T Waves, U Waves, PR Intervals, QT Intervals, ST Segments, Isoelectric lines, and any other data understood by someone affluent in the art. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. ECG signals may provide information about different phases of cardiac electrical activity that may indicate abnormalities in the heart. At least a signal from the corpus of ECG signals may have a corresponding meaning, which in a nonlimiting embodiment can form a (ECG signal, corresponding meaning) pair. In a nonlimiting embodiment, a first ECG signal may have a first corresponding meaning, e.g., a first corresponding categorical value of a certain disease condition (for example, CHD—representing congenital heart disease), and/or a first corresponding sequence (for example—a sentence such as "the patient may have congenital heart disease"). In some embodiments, the corpus of ECG signals and the corresponding meaning may be accessed by the processor, such as processor 112. In some embodiments, an ECG signal may be accessed by one or more ECG devices, such as at least an ECG device 104. In a nonlimiting embodiment, additional processed may be needed to perform access of the corpus of ECG Signals, as described further below. Aggregate ECG data repository 136 may also include historical ECG records, (ECG, text) pairs, (ECG, echocardiogram) pairs, patient notes, labeled ECG data, unlabeled ECG data, learned ECG data, raw ECG data, normalized ECG data, patient data, and the like. Aggregate ECG data repository 136 may be received through Processor 112, at least an ECG device 104, or any other system/device discussed in the application. In a non-limiting embodiment, signals may also comprise electroencephalogram signals, electrooculogram signals, magnetoencephalogram signals, evoked potentials, galvanic skin response signals, near-infrared spectroscopy signals, and the like.

With continued reference to FIG. 1, processor 112 may execute a processing pipeline 144 wherein the processing pipeline is configured to generate an output as a function of the aggregate ECG data repository 136. As used herein, "processing pipeline" refers to a series of systematic steps or a workflow that data goes through from its initial raw form to a format suitable for building and using machine learning model. The processing pipeline typically encompasses several stages, each designed to handle specific aspects of data preparation, model training and deployment. In a non-limiting embodiment, processing pipeline 144 may include gathering data from various sources, such as the aggregate ECG data repository 136, handling and preprocessing raw data, removing outliers, normalizing data, encoding categorical variables, creating new features from existing data for enhanced data prediction, splitting data into training, validation and testing sets, selecting appropriate machine learning algorithms and training data, assessing a machine-learning model's performance, adjusting a machine-learning model's parameters to improve performance, monitoring a machine learning model's performance, and the like. Processing pipeline 144 may be configured to incorporate feedback and learnings from any deployed machine learning models to refine data processing, feature engineering, and the like. In a non-limiting embodiment, processing pipeline may be configured to generate output data based on one or more ECG records. During execution of processing pipeline, processor 112 may execute a quantizing model 148. Quantizing model is a derivative type of generative model. Quantizing model quantizes input data from the aggregate ECG data repository (such as an ECG signal) by tokenization into a fixed set of vectors. The vectors are drawn from a fixed vocabulary capable of representing any data from the aggregate ECG data repository. The fixed vocabulary capable of representing input data from the aggregate ECG data repository may be derived by training the quantizing model with a plurality of input data from the aggregate ECG data repository. For example, the fixed vocabulary capable of representing any ECG signal may be derived by training the quantizing model with a plurality of ECG signal.

With continued reference to FIG. 1, during execution of the processing pipeline 144, processor 112 may execute an autoregressive model 152 to transform the input data from the aggregate ECG data repository according to a specified requirement. The autoregressive (AR) model is a feedforward model which predicts future output values from historical output values. As used herein a "feed forward model" refers to a machine learning model, such as a neural network, that is organized in layers that consist of nodes and each node is connected to every node in the next layer. An AR model is a representation of a type of random process; as such, it is used to describe certain time-varying processes in nature, economics, behavior, etc. The autoregressive model specifies that the output variable depends linearly on its own previous values and on a stochastic term (an imperfectly predictable term).

Still referring to FIG. 1, a basic equation for an autoregressive model of order p (denoted as AR(P)) is as follows:

$$Xt = c + \phi 1 Xt-1 + \phi 2 Xt-2 + \ldots + \phi p Xt-p + \epsilon t$$

Xt: Current value of the time series at time t.
c: Constant term (also known as the intercept). $\phi 1$, $\phi 2, \ldots, \phi p$: Coefficients of the model. These parameters measure the influence of the p previous time series values on the current value. Xt−1, Xt−2, . . . . Xt−p: Previous p values of the time series. $\epsilon_t$: Error term at time t, which is assumed to be white noise (i.e., normally distributed with zero mean and constant variance)

In this model, p may determine a number of lagged observations included in the model, which is why it's referred to as the order of the model. Coefficients $\phi 1$, $\phi 2, \ldots, \phi p$ are estimated from the data, typically using methods like least squares.

Still referring to FIG. 1, these connections may be weighted and may represent the strength of the connection. This concept is discussed in greater detail below. In a non-limiting embodiment, the AR model 152 may be used to predict future values based on historical values of a time series data. In an AR model, the value of a time series at a given point in time is regressed on its own past values. Specifically order p of the AR model, denoted as AR(p), p represents the number of previous values used to make the prediction. AR models are a type of sequence model that maps sequence to sequential data such as scalars (e.g., language models) and sequences (e.g., machine translation models) or even to non-sequential data such as images. In a non-limiting embodiment, an AR language model (e.g., the GPT-n family) takes texts as input (i.e. "conditioning" the model on at least an input text) and transforms the text into a sequence of numeric token and then one-hot vectors. As used herein a "one-hot vector" is a vector that represents categorical variables as binary vectors. The one-hot vector then is posted into strings of text by a predefined mapping that is the inverse of the mapping going from text to tokened used to encode text.

With reference to FIG. 1, during execution of processing pipeline 144, processor 112 may execute a contrastive learning model 156. As used herein "contrastive learning" is a machine learning paradigm where unlabeled data points are juxtaposed against each other to teach a model which points are similar, and which are different. In other words, the training data is contrasted against each other. Those belonging to the same distribution are pushed towards each other in the embedding space, while those belonging to different distributions are pulled against each other. In non-limiting embodiments, contrastive learning may be applied to supervised and unsupervised machine learning processes.

With reference to FIG. 1, during execution of processing pipeline 144, processor 112 may be configured to execute a sequence-to-sequence model 160. Sequence-to-sequence learning comprises training models to convert sequences from one domain (e.g., sentences in English) to sequences in another domain (e.g. same sentences translated to French). For example, the sequence-to-sequence model may include an encoder-decoder pair.

With continued reference to FIG. 1, processor 112 generates a generative model 166 as a function of the plurality of ECG images 132 and the aggregate ECG data repository 136. As used herein a "generative model" is a machine learning model designed to generate new data based on a given dataset. Generative models may aim to understand and replicate the underlying distribution of data. A generative model may be a machine learning model that can generate new data after learning from a dataset. Non-limiting embodiments of generative models may include Generative Adversarial Networks (GANs), Variational Autoencoders (VAEs), Diffusion models, Autoregressive Models and the like. Processor 112 may generate a generative model 166 as a function of the at least a discrepancy where the generative model 166 may include training the generative model using generative training data where the generative training data correlates at least an ECG signal from the corpus of ECG signals as an input to an output of echocardiogram datum. In a non-limiting embodiment, the generative model training data may comprise at least a plurality of ECG images as an input. In another non-limiting embodiment, the generative model training data may comprise at least an aggregate ECG data repository as input.

Continuing to refer to FIG. 1, Processor 112 may use user feedback to train the models described above. For example, generative model 166 may be trained using past inputs and outputs of generative model. In some embodiments, if user feedback indicates that an output of the generative model was "bad," then that output and the corresponding input may be removed from training data used to train generative model, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of generative model 166 may include user feedback.

With continued reference to FIG. 1, in some embodiments, an accuracy score may be calculated for generative model using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; computing device 120 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

With continued reference to FIG. 1 in one or more embodiments, computing device may implement one or more aspects of "generative artificial intelligence (AI)," a type of AI that uses machine learning algorithms to create, establish, or otherwise generate data such as, without limitation the plurality of ECG images and/or the like in any data structure as described herein (e.g., text, image, video, audio, among others) that is similar to one or more provided training examples. In an embodiment, machine learning module described herein may generate one or more generative machine learning models that are trained on one or more set of generative training data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, "generative models" refers to statistical models of the joint probability distribution $P(X, Y)$ on a given observable variable x, representing features or data that can be directly measured or observed (e.g., the plurality of ECG images) and target variable y, representing the outcomes or labels that one or more generative models aims to predict or generate (e.g., echocardiogram data). In some cases, generative models may rely on Bayes theorem to find joint probability; for instance, and without limitation, Naïve Bayes classifiers may be employed by computing device to categorize input data such as, without limitation, the plurality of ECG images into different categories such as, without limitation, conditioned, unconditioned, and the like.

In a non-limiting example, and still referring to FIG. 1, one or more generative machine learning models may include one or more Naïve Bayes classifiers generated, by computing device, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing Device may then calculate a likelihood table by calculating probabilities of different data entries and classification labels. Computing device may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)ΠiP(Xi|Y), wherein P(Y) may be the prior probability of the class, and P(X$_i$|Y) is the conditional probability of each feature given the class. One or more generative machine learning models containing Naïve Bayes classifiers may be trained on labeled training data, estimating conditional probabilities P(X$_i$|Y) and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature Xi, sample at least a value according to conditional distribution P(X$_i$|y). Sampled feature values may then be combined to form one or more new data instance with selected class label y. In a non-limiting example, one or more generative machine learning models may include one or more Naïve Bayes classifiers to generate new examples of echocardiogram data based on the aggregate ECG data repository (e.g., conditioned, unconditioned, and the like) wherein the models may be trained using training data containing a plurality of features e.g., features of the plurality of ECG images", and/or the like as input correlated to a plurality of labeled classes e.g., classifications of aggregate ECG data repository as output.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 12.

With continued reference to FIG. 1, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 12 to distinguish between different categories e.g., real vs. fake or states e.g., TRUE vs. FALSE within the context of generated data such as, without limitations, echocardiogram data, and/or the like. In some cases, computing device may implement one or more classification algorithms such as, without limitation, Support Vector Machines (SVM), Logistic Regression, Decision Trees, and/or the like to define decision boundaries.

In a non-limiting example, and still referring to FIG. 1, generator of GAN may be responsible for creating synthetic data that resembles real echocardiogram data. In some cases, GAN may be configured to receive an aggregate ECG data repository such as, without limitation, ECG signals, patient data, and the like, as input and generates corresponding echocardiogram data containing information describing or evaluating the performance of one or more ECG signals]. On the other hand, discriminator of GAN may evaluate the authenticity of the generated content by comparing it to real echocardiogram data, for example, discriminator may distinguish between genuine and generated content and providing feedback to generator to improve the model performance.

With continued reference to FIG. 1, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 1, VAE may be used by computing device to model complex relationships between the plurality of ECG images and the aggregate ECG data repository e.g., ECG signals, patient data, historical ECG signal values, and the like. In some cases, VAE may encode input data into a latent space, capturing echocardiogram data. Such encoding process may include learning one or more probabilistic mappings from observed aggregate ECG data repository to a lower-dimensional latent representation. Latent representation may then be decoded back into the original data space, therefore reconstructing the plurality of ECG images. In some cases, such decoding process may allow VAE to generate new examples or variations that are consistent with the learned distributions.

Still referring to FIG. 1, computing device may configure generative machine learning models to analyze input data such as, without limitation, the plurality of ECG images to one or more predefined templates such as unconditioned ECG images representing correct ECG images without any abnormalities described above, thereby allowing computing device to identify discrepancies or deviations from the plurality of received ECG images. In some cases, computing device may be configured to pinpoint specific errors in the plurality of ECG images or any other aspects of the aggregate ECG data repository. In a non-limiting example, computing device may be configured to implement generative machine learning models to incorporate additional models to detect any abnormalities in received ECG images. In some cases, errors may be classified into different categories or severity levels. In a non-limiting example, some errors may be considered minor, and generative machine learning model such as, without limitation, GAN may be configured to generate echocardiogram data contain only slight adjustments while others may be more significant and demand more substantial corrections. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 1, in some cases, computing device may be configured to identify and rank detected common deficiencies across plurality of ECG images/for instance, and without limitation, one or more machine learning models may classify errors in a specific order. Such ranking process may enable a prioritization of most prevalent issues, allowing instructors or computing device to address the issue or discrepancy.

Still referring to FIG. 1, in some cases, one or more generative machine learning models may also be applied by computing device to edit, modify, or otherwise manipulate existing data or data structures. In an embodiment, output of training data used to train one or more generative machine learning models such as GAN as described herein may include generative model training data that linguistically or visually demonstrate modified the aggregate ECG data repository e.g., ECG data signals, and/or the like. In some cases, echocardiogram data may be synchronized with the plurality of ECG images for example, and without limitation, in a particular setting, for example: "a side-by-side or even overlayed arrangement with the input user action data, providing real-time visual guidance". Additionally, or alternatively, discrepancies between the plurality of ECG images may be generated using generative machine learning models to address possible differences between ECG images. In some cases, such echocardiogram may be integrated with the aggregate ECG data repository, offering user a multi-sensory instructional experience.

Additionally, or alternatively, and still referring to FIG. 1, computing device may be configured to continuously monitor the aggregate ECG data repository. In an embodiment, computing device may configure discriminator to provide ongoing feedback and further corrections as needed to subsequent input data (e.g., the plurality of ECG images). In some cases, one or more sensors such as, without limitation, wearable device, motion sensor, or other sensors or devices described herein may provide aggregate ECG data repository information that may be used as subsequent input data or training data for one or more generative machine learning models described herein. An iterative feedback loop may be created as computing device continuously receive real-time data, identify errors as a function of real-time data, delivering corrections based on the identified errors, and monitoring device response signal on the delivered corrections. In an embodiment, computing device may be configured to retrain one or more generative machine learning models based on the plurality of ECG images 132 or update training data of one or more generative machine learning models by integrating echocardiogram data into the original training data. In such embodiment, iterative feedback loop may allow machine learning module to adapt to an updated aggregate ECG data repository, enabling one or more generative machine learning models described herein to learn and update based on at least autoregressive models, quantizing models, and the like and generated feedback.

With continued reference to FIG. 1, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models that may be used to output echocardiogram data.

Still referring to FIG. 1, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate output echocardiogram data. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models may be used to output echocardiogram data described herein. As an ordinary person skilled in the art, upon reviewing the entirety of this disclosure, will be aware of various multi-model neural network and combination thereof that may be implemented by apparatus 100 in consistent with this disclosure.

Referring now to FIGS. 2A-D, FIGS. 2A-D illustrate diagrams of methods for training systems capable of generating an output based on an ECG device. In a non-limiting embodiment, the trained system may take an ECG signal as the input and generate a scalar value and/or a sequence normally derived from an ECHO. The scalar value and/or a sequence may be used for disease diagnosis. The scalar value may include categorical value of a certain disease condition (e.g., congenital heart disease (CHD)). A sequence may include a sentence such as "the patient may have congenital heart disease."

In some embodiments, and still referring to FIGS. 2A-D, the training process may include feeding raw or normalized ECG data to train an AR model, e.g., as described in method 200b. To leverage the in-context learning, the AR model may be also trained with text descriptions to improve the model's generative performance. The text descriptions may be associated with ECG data, or any knowledge about ECG serialized into a sequence, including but not limited to standardized codes describing disease conditions, diagnosis codes, ontologies etc. After fine-tuning the AR model with prompts, the AR model may be used to generate a scalar value and/or a sequence normally derived from an ECHO.

In some embodiments, and still referring to FIGS. 2A-D, the training process may also include preprocessing the raw or normalized ECG data before feeding the ECG data to the AR model. For example, the raw or normalized ECG data may be fed to a quantizing model, e.g., as described in method 200a and/or a linear projection model, as described in method 200c. As such, the quantizing model and/or the linear projection model may be used to compress the ECG data (e.g., by reducing the dimensionality of the ECG data), thus reducing the computational overhead of the downstream tasks. As the other example, the raw or normalized ECG data may be fed to a contrastive learning model, e.g., as described in method 200d. The contrastive learning model may be used to compensate for the training data scarcity, and to achieve better performance of the AR model.

Figure 2A:
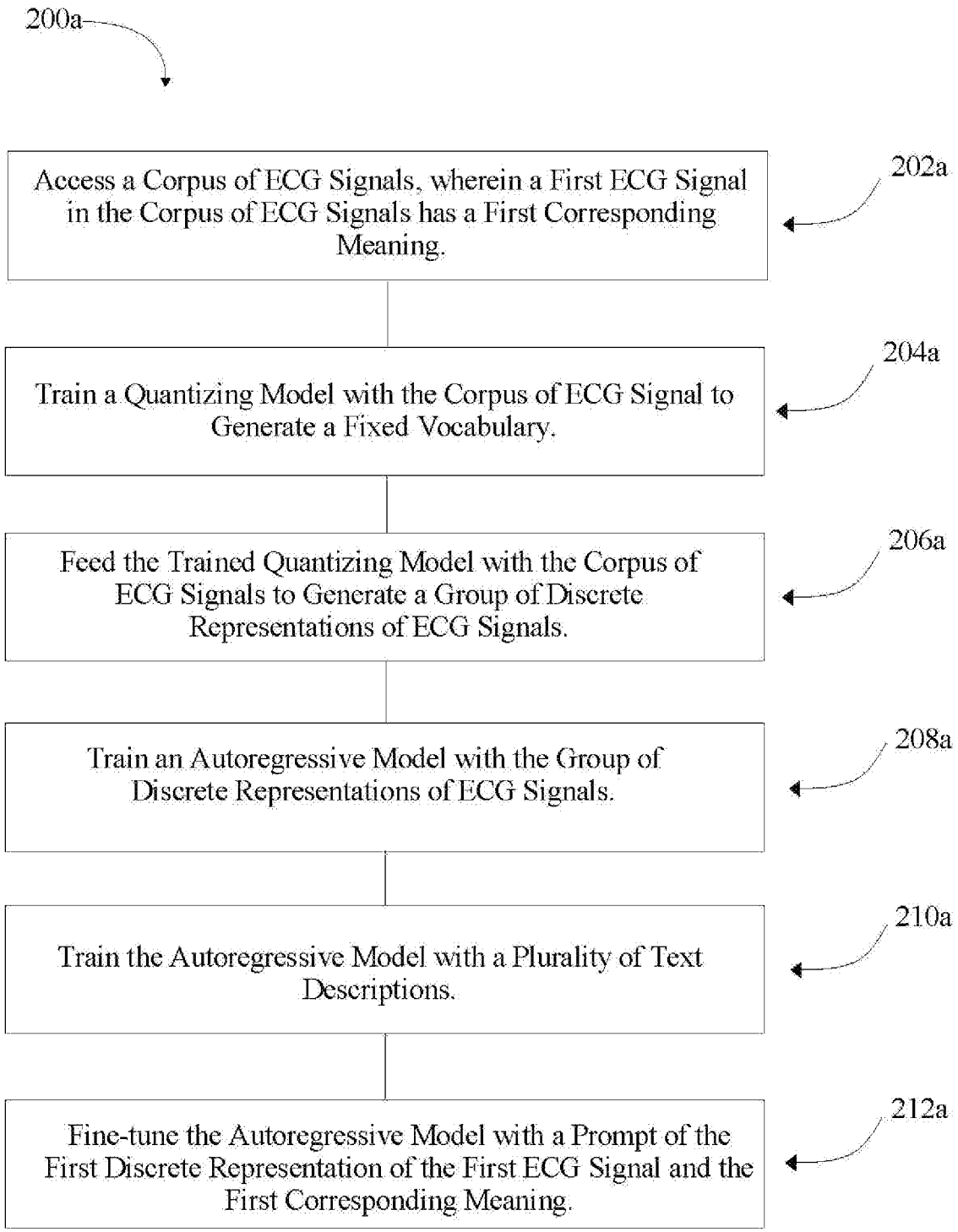
FIG. 2A-2D is a diagrammatic representation of a method for training a system capable of generating an output based on an ECG device, in accordance with certain embodiments of the present disclosure.

FIG. 2A illustrates a simplified diagram of a method 200a for training a system capable of generating an output based on an ECG device, such as the at least an ECG device 104, in accordance with certain embodiments of the present disclosure. According to some embodiments consistent with FIG. 1, method 200a may be performed by a computer processor, such as processor 112 based on instructions and/or data stored in a memory, such as memory 116.

Referring to FIG. 2A, at process 202a, a corpus of ECG signals is accessed. At least one ECG signal in the corpus of ECG signals may have a corresponding meaning, thus forming a (ECG signal, corresponding meaning) pair. For example, a first ECG signal may have a first corresponding meaning, e.g., a first corresponding categorical value of a certain disease conditions (e.g., CHD representing congenital heart disease), and/or a first corresponding sequence (e.g., a sentence such as "the patient may have congenital heart disease"). In some embodiments, the corpus of ECG signals and the corresponding meaning may be accessed by the database, such as database 104. In some embodiments, the ECG signal may be accessed by one or more ECG devices 101-103 directly. In some embodiments, additional processes need to be performed to access the corpus of ECG signals, as described with reference to FIG. 3.

Referring to FIG. 2A, at a process 204a, a quantizing model, such as the quantizing model 142, is trained with the corpus of ECG signals as an input, to generate a fixed vocabulary. The parameters of the quantizing model are updated using backpropagation over each iteration. In some embodiments, the quantizing model 142 may be a VAE. For example, the quantizing model may be a VQ-VAE model or a VQ-GAN model.

Referring to FIG. 2A, as discussed above, an at process 204a, VAE includes an encoder, a decoder and a loss function. The corpus of ECG signals will be fed to the encoder and decoder to reconstruct the corpus of ECG signals. For example, the encoder may represent the first ECG signal as a representation of the first ECG signal, and the decoder will take the representation of the first ECG signal as an input to reconstruct the first ECG signal. After training, the decoder may be discarded and a fixed vocabulary (e.g., a codebook) may be generated in the encoder. The encoder may use the fixed vocabulary to represent any ECG signal as a discrete representation of that ECG signal, e.g., a fixed set of learned vectors.

Referring to FIG. 2A, at process 206a, the trained quantizing model is fed with the corpus of ECG signals to generate a group of discrete representations of ECG signals. After training, the quantizing model may use the fixed vocabulary to represent any ECG signal as a discrete representation of that ECG signal, e.g., a fixed set of learned vectors. Specifically, for each ECG signal in the corpus of ECG signals, the trained quantizing model may tokenize one ECG signal into a series of tokens (e.g., a series of integers) and generate a fixed learned vector (e.g., a feature vector) for each token. As such, the ECG signal may be represented as a fixed set of learned vectors. For example, the fixed vocabulary may be used to represent the first ECG signal as a first discrete representation of the first ECG signal (e.g., a fixed set of learned vectors). The trained quantizing model may perform similar process for other ECG signals among the corpus of ECG signals to derive the group of discrete representations of ECG signals. As an autoencoder, the quantizing model may compress the high-dimension data into a low-dimension data (e.g., a latent representation). The corpus of ECG signals may be compressed into the group of discrete representations of ECG signals which may be used to reduce the computational overhead of the downstream tasks. For example, the group of discrete representations may be used as the training data for an autoregressive model to reduce the computational overhead.

Referring to FIG. 2A, at process 208a, an autoregressive (AR) model, such as the autoregressive model 144, is trained with the group of discrete representations of ECG signals. After training, the AR model may represent any ECG signal as a discrete representation of that ECG signal, e.g., a fixed set of learned vectors. For example, the first ECG signal may be represented as a first discrete representation of the first ECG signal. The group of discrete representation of ECG signals may be produced by the quantizing model as described above. As described in the process 206, a discrete representation of ECG signal may be a fixed set of learned vectors. Hence for each discrete representation of ECG signal, the AR model may by trained by tokenizing the discrete representation of ECG signal into a series of tokens (e.g., a series of integers) and updating the parameters of the AR model. The parameters of the AR model may be updated by predicting the next token based on previous sequence of tokens, and the number of previous tokens may be determined by the order p. The trained AR model may output a second discrete representation of the ECG signal. For example, the AR model may tokenize the first representation of the first ECG signal into a series of tokens (e.g., a series of vectors), and predict the next token (e.g., a vector) as an output based on the series of previous tokens. As such, the first representation of the first ECG signal may further be represented as a second discrete representation of the first ECG signal.

Referring to FIG. 2A, Electrocardiogram (ECG) is widely used in clinical diagnosis to provide information about cardiac disease according to its three different components: P wave, QRS complex, and T wave in different conditions [1]. The characteristics of these waveforms are of great importance for the classification of the ECG signals and the diagnosis of cardiovascular disease.

Referring to FIG. 2A, deep learning based models [2, 3, 4, 5, 6, 7] have been used for ECG classification, giving state-of-the-art performance. According to how the information is exploited, these approaches can be divided into two categories: methods based on convolutional neural network (CNN) and methods based on sequence module. The CNN-based methods aim to exploit morphological features of ECG signals either in one dimensional time series [2, 3] or in two dimensional image [4] and are shown to outperform the traditional machine learning methods such as support vector machines (SVM)[8, 9, 10, 11]. However, these methods focus on the morpho-logical features in the area centered around a certain peak data point or in the wavelets decomposed from original signal via DWT [3], and they are ineffective in exploiting the latent feature of the temporal signal in either time or frequency domain. In contrast, the methods with sequence module structure often employ recurrent neural network (RNN) based models, such as long-short term memory (LSTM) [5, 6] or gated recurrent unit (GRU) [7], to capture the latent temporal information of the ECG signals for classification.

Continuing reference to FIG. 2A, The transformer model has been proposed and applied to many applications including ECG classification [12], giving state-of-the-art performance [13]. In [12], a transformer based method, i.e., FusingTF, is presented for ECG classification, where the ECG signal is represented in a high-dimensional space (i.e., 64-D) via a simple 1-D convolutional layer to expand the original dimension (i.e., 1-D) for the transformer. After this, a positional encoder is applied to incorporate additional temporal information into the 64-D result, however, this method is limited in compensating for the loss of temporal information within the signal caused by the 1-D CNN. In addition, the high-dimensional embedding will result in a model with increased number of parameters. Although the original ECG signal could be used directly as the transformer input, the presence of noise in the signal can degrade the classification performance. Representing the ECG signal in the embedding space can help denoise the signal and reduce the number of parameters in the model.

Continuing reference to FIG. 2A, a low-dimensional denoising embedding transformer model (LDTF) for ECG classification, which improves the performance with fewer training parameters by introducing a low-dimensional denoising embedding (LDE) approach for signal embedding and a deeper and narrower transformer model for signal classification. The proposed method includes two stages, namely, low-dimensional denoising embedding and transformer learning. First, the original ECG signal is represented in a low-dimensional space by the LDE approach, which employs discrete wavelet transform (DWT) [6, 14, 15] and fast Fourier transform (FFT) to exploit the features from both time domain and frequency domain simultaneously.

Continuing reference to FIG. 2A, The DWT of ECG signal can effectively expand the dimension of the original ECG signal and extract the primary features of the signal in time domain thereby preserving the temporal information of the signal, whereas FFT generates the features of the ECG signal in the frequency domain. In-stead of mixing different kinds of features obtained above, we integrate them together by representing each feature with a specific dimension in the low-dimensional space. Such that, the LDE method can well preserve the characteristics of ECG signals. Then, with the low-dimensional embedding results for transformer learning, we can thereby use a narrower and deeper structure by stacking more transformer encoder layers to improve the classification performance with fewer training parameters in each layer.

Continuing reference to FIG. 2A, DWT is used to decompose and reconstruct the original ECG signal to get its waveform representations in time domain, which aims to preserve the signal's own temporal information. For the purpose of a more comprehensive representation of the signal, fast Fourier transform is also adopted to extract features of the signal (i.e., magnitude and phase angle) in frequency domain. Then, we can obtain a low-dimensional embedding representation for transformer learning by concatenating the DWT decomposed wavelets, reconstructed signal, the original ECG signal and its magnitude and phase angle. As this representation already contains the information from both time and frequency domain, there is no need to use other function as in to add additional temporal information to the embedding result. The details of the LDE method is given as follows.

Let $X \in R^{2 \times l}$ be the two leads ECG signal and $X_c \in R^{1 \times l}$ be one lead of the ECG signal, where $c \in \{1, 2\}$ is the channel number and l is the length of the signal. Then, it can be decomposed to wavelets via DWT, as follows:

$$x_{c,j,H}[n] = \sum_{k=0}^{K-1} x_{c,j-1,H}[2n-k]h(k)$$

$$x_{c,j,L}[n] = \sum_{k=0}^{K-1} x_{c,j-1,L}[2n-k]g(k)$$

where n denotes the n-th element of the signal and K is the length of slide window, $k \in \{0, \ldots, K-1\}$. Here, $h(\cdot)$ and $g(\cdot)$ denote the high pass filter and low pass filter, respectively. $x_{c,j,H}$ and $x_{c,j,L}$ are the decomposing results at j-th level of $h(\cdot)$ and $g(\cdot)$ respectively, where $j \in \{1, 2, 3, 4\}$. Then, we can obtain the denoised reconstruction signal $\hat{x}_c$ with an inverse decomposition operation as follows:

$$\hat{x}_{c,j-1,H} = \sum_{k=0}^{K-1} \hat{x}_{c,j-1,H}[2n-k]h(k) + \sum_{k=0}^{K-1} x_{c,j-1,L}[2n-k]g(k)$$

when j=1, we will obtain the reconstructed signal $\hat{x}_c = \hat{x}_{c,0,H}$.

To obtain a better representation of the signal, we also ex-tract the information from frequency domain, where the magnitude $z_c \in R^{1 \times l}$ and the phase angle $\varphi_c \in R^{1 \times l}$ of the signal $x_c$ are used as parts of the embedding result, which are obtained respectively, as follows:

$$z_c = |ff_t(x_c)|$$

$$\varphi_c = \text{angle}(ff_t(x_c))$$

where $ff_t(\cdot)$ denotes the fast Fourier transform operation. Here, $|\cdot|$ and $\text{angle}(\cdot)$ denote the calculation of absolute value and phase angle respectively. Finally, we can obtain a low-dimensional embedding result $x_{lde} \in R^{d \times l}$ by concatenating the two leads original ECG isngla,s decomposed wavelets, reconstructed signals, and magnitudes and phase angels, which is expressed as follows:

$$X_{lde} = [x_1; x_{1,1,L}; \ldots ; x_{1,4,L}; x_{1,4,H}; \hat{x}_1; z_1; \varphi_1; x_2;$$
$$x_{2,1,L}; \ldots ; x_{2,4,L}; x_{2,4,H}; \hat{x}_2; z_2; \varphi_2]$$

Here the dimension d of $X_{lde}$ is 18. Because of integrating different features in different dimensions separately, the latent features of $X_{lde}$ can be more easily learned by the transformer model.

Referring to FIG. 2A, Regarding transformer learning stage, thanks to the low dimensional embedding result as the input, we can obtain a narrower and deeper structure with less training parameters for ECG classification. This is because here the space consumed mainly comes from the fully forward connected net-work structure (i.e., feed forward block) in each transformer encoder layer. Therefore, with the low-dimensional input, the training parameters of each transformer encoder layer will be reduced rapidly. Such that, we can stack more transformer encoder layers with fewer parameters (i.e., 9,258,742) in each layer, and fewer parameters (i.e., 74,087,228) for the whole model. Whereas the similar study in [12], i.e., FusingTF, has 32,029,382 parameters in each transformer encoder layer, and a total number of 192,237,988 parameters.

The transformer learning part of the model consists of 8 transformer encoder layers and one transformer classifier layer. Each transformer encoder layer includes one multi-head attention block (MAB) with 6 heads, one feed forward block (FFB) and two add and norm blocks (ANB).

Assuming Y is the input of MAB in each transformer encoder layer, which is initially set as $Y = X_{lde}$. Then, the linear mapping result $YW_{i,q}$ of Y via transform matrix $W_{i,q} \in R^{l \times l}$ can be used to calculate the attention result $H_i \in R^{d \times l}$ of the i-th head, where $i \in \{1, \ldots, 6\}$ and $q \in \{1,2,3\}$. Such that $H_i$ can be obtained as follows:

$$H_i = softmax\left(\frac{(YW_{i,1})(YW_{i,2})^T}{\sqrt{d}}\right)(YW_{i,3})$$

Where T denotes the transposition operation, and the softmax function is used to calculate the weights on the linear mapping result $YW_{i,3}$.

To integrate the attention results of all heads, here we perform another linear mapping operation via transform matrix $W_o \in R^{6l \times l}$, then the output of MAB can be obtained as follows:

$$O_{MAB} = [H_1, \ldots, H_i, \ldots, H_6]W_o$$

After that, a residual connection and layer norm operation are conducted in ANB to connect the FFB, here the FFB consists of two fully connected layers with a rectified linear unit (ReLU). Them, with an ANB again after the FFB, the output is obtained of the transformer encoder layer or the transformer classifier layer that contains one fully connected layer and a softmax function.

Referring to FIG. 2A, at a process 210a, the AR model, such as the autoregressive model 144, is trained with a plurality of text descriptions. The parameters of the AR model are updated in this stage. In some embodiments, the AR model is trained with both the group of discrete representations of ECG signals and the plurality of text descriptions.

Referring to FIG. 2A, the rich capabilities that emerge in large parameter language models with autoregressive modeling, such as "in-context learning", an inference time capability, have not been leveraged to date for ECG signals. The generative capacity inherent in AR training in large part is responsible for this powerful capability of large language models—the model learns a task even during inference time from examples crafted as model prompt inputs. Given the relatively large amount of ECG data that is available, this modeling can yield a model with in-context learning capabilities if the training budget (amount of data) is commensurate with the large model size.

Referring to FIG. 2A, to leverage the in-context learning, the AR model may be trained with a plurality of text descriptions to improve the model's generative performance. In some embodiments, the plurality of text descriptions is associated with one or more ECG signal in the corpus of ECG signals, such as by describing a disease condition in categorical form. For example, the corresponding categorical value of the first ECG signal (e.g., a classification code CHD) may be used as text description for training the AR model. However, since the amount of ECG and text description pairs are relatively scarce where the text description is harvested from structured or unstructured text (e.g. patient notes), in some embodiments, the plurality of text descriptions is not associated with the ECG signal. As such, the plurality of text description could be any knowledge about ECG serialized into a sequence, including but not limited to standardized codes describing disease conditions, diagnosis codes, ontologies etc. The plurality of text description may be unstructured data (e.g., a patient notes) and/or structured data such as tables serialized into sentences.

Referring to FIG. 2A, At process 212a, the AR model is fine-tuned with a prompt including the discrete representation of the first ECG signal and the first corresponding meaning. The fine-tuned autoregressive model can generate an output normally detectable by analyzing an ECHO image. The parameters of the AR model are updated in this stage. The fine-tuned AR model may generate an output, such as output 190, which is normally detectable by analyzing an ECHO image. For example, the AR model may add a classification head that converts the discrete representation of the first ECG signal to the output.

Referring to FIG. 2A, ECHO tests are performed relatively infrequently compared to ECGs in large part due to the higher cost. But in the eyes of seasoned electrophysiologists, ECGs may contain sufficient information to detect at least some if not almost all disease conditions that are normally detected using an ECHO. An example study on the correlation of ECG features and L VEF (detected in Electrocardiography) disclosed in Kyndaron Reinier et. al, Electrical surrogate for detection of severe left ventricular systolic dysfunction, 2018, which is incorporated herein by reference in its entirety. Also, the amount of available ECG data exceeds the amount of ECHO data, and the amount of (ECG, ECHO) pairs is relatively scarce, where pairing is done when both these tests are done within a time window (e.g., within one month). Hence there is a desire to further exploit the information hidden in ECG. An example application of extracting information in ECG is disclosed in Annamalai Natarajan et. al, Convolution-Free Waveform Transformers for Multi-Lead ECG Classification, Computing in Cardiology—2021 PhysioNet Challenge, 2021, which is incorporated herein by reference in its entirety. The convolutional front-end subnetwork comprises two convolutional layers, each directly followed by a ReLU activation and a maxpooling layer. The convolutional layers are followed by a reshape layer to flatten the last dimension. The role of the convolutional subnetwork is to extract spatiotemporal features from raw input ECG signals and feed them to the encoder. Since using a multi-head component (which will come later) results in loss of ordering in the input sequence, a piece of information needs to be added to the embeddings to give the encoder some sense of order. Here, a positional encoder may be used and add its output to the embeddings obtained from the re-shape layer before supplying them to the transformer encoder. Next, the encoder consists of a multi-head, self-attention layer, followed by a dropout and a layer normalization, then a fully connected feed-forward network, and finally a dropout and a layer normalization. scaled dot-product attention may be used where a query, key, and value vectors are generated. These vectors are created for each input by multiplying the input by Wq, Wk, and Wv, which are learned weight matrices for query, key, and value, respectively. The queries, keys, and values are individually stacked to create Q, K, and V, respectively. The attention values may then be computed as $$\text{Attention } (Q, K, V) = \text{softmax}\left(\frac{QK^T}{\sqrt{d_k}}\right)V,$$

where $Q \in R^{n \times dq}$, $K \in R^{n \times dk}$, and $V \in R^{n \times vk}$. Here, n is the length of the sequence, and dq, dk, and dv are the embedding dimension of Q, K, and V, respectively. The scaling factor $\sqrt{dk}$ is added to mitigate the softmax's small gradient when its argument is very large. We use four of these components in the transformer encoder. Embeddings generated by the transformer encoder are flattened and fed to three FC layers where each of the first two FC layers is followed by a Rectified Linear Unit (ReLU) activation function and the third one is followed by a sigmoid function for achieving binary classification.

Continuing reference to FIG. 2A, one alternative is to use the AR model to generate an output based on the ECG signal, while the output is normally detectable from an ECHO. The AR model may be trained to output such scalar value as classification code, categorical value, numeric value describing disease conditions. The AR model may be trained to output a sequence of information such as a sentence describing a disease condition, a 1-D waveform when the ECHO is operated under the motion mode (M-mode). Such scalar value and sequences of information are representative of information normally detectable from analyzing an ECHO image. The doctors may use such scalar value and/or a sequence of information for diagnosis.

In some embodiments, the discrete representation of the first ECG may be generated at the process 206, and/or the process 208 described above. The corresponding meaning of the ECG signal may be represented as a categorical value representing a certain disease condition, and/or a corresponding sequence of information. This sequence of information could be any sequence, e.g., a sentence describing a disease condition, a numerical sequence representing a I-D M-mode signal, a 1-D M-mode waveform etc. The discrete representations of other ECG signals derived by the corpus of ECG signals and their corresponding meaning may also be used to fine-tune the AR model to achieve the desired output and performance. For example, the discrete representation of the first ECG signal may be (a) the first representation of the first ECG signal generated by the trained quantizing model at the process 206, (b) the second representation of the first ECG signal generated by a combination of the trained quantizing model and the trained AR model at the process 206 and the process 208, and/or (c) the first representation of the first ECG signal generated by the trained AR model alone at the process 208. Further, the corresponding meaning of the first ECG signal may be CHD.

As described above, and with reference to FIG. 2A, this kind of fine-tuning leverages the models generated by some or all of the processes described above to compensate for the scarcity of labeled (ECG, text) pairs. Further, since the learning process, as well as model architecture for the AR model is the same both during pretraining and fine-tuning stages, learning a new task with fine-tuning often requires an order of magnitude less labeled data compared to traditional fine-tuning of a pretrained model where new weights from architectural additions have to be learned from scratch in addition to pretrained model weight updates. In some embodiments, the trained quantizing model and/or the fine-tuned AR model may be executed with a particular ECG signal as an input to generate an output, such as output 190, which is normally detectable by analyzing an ECHO image.

Figure 2B:
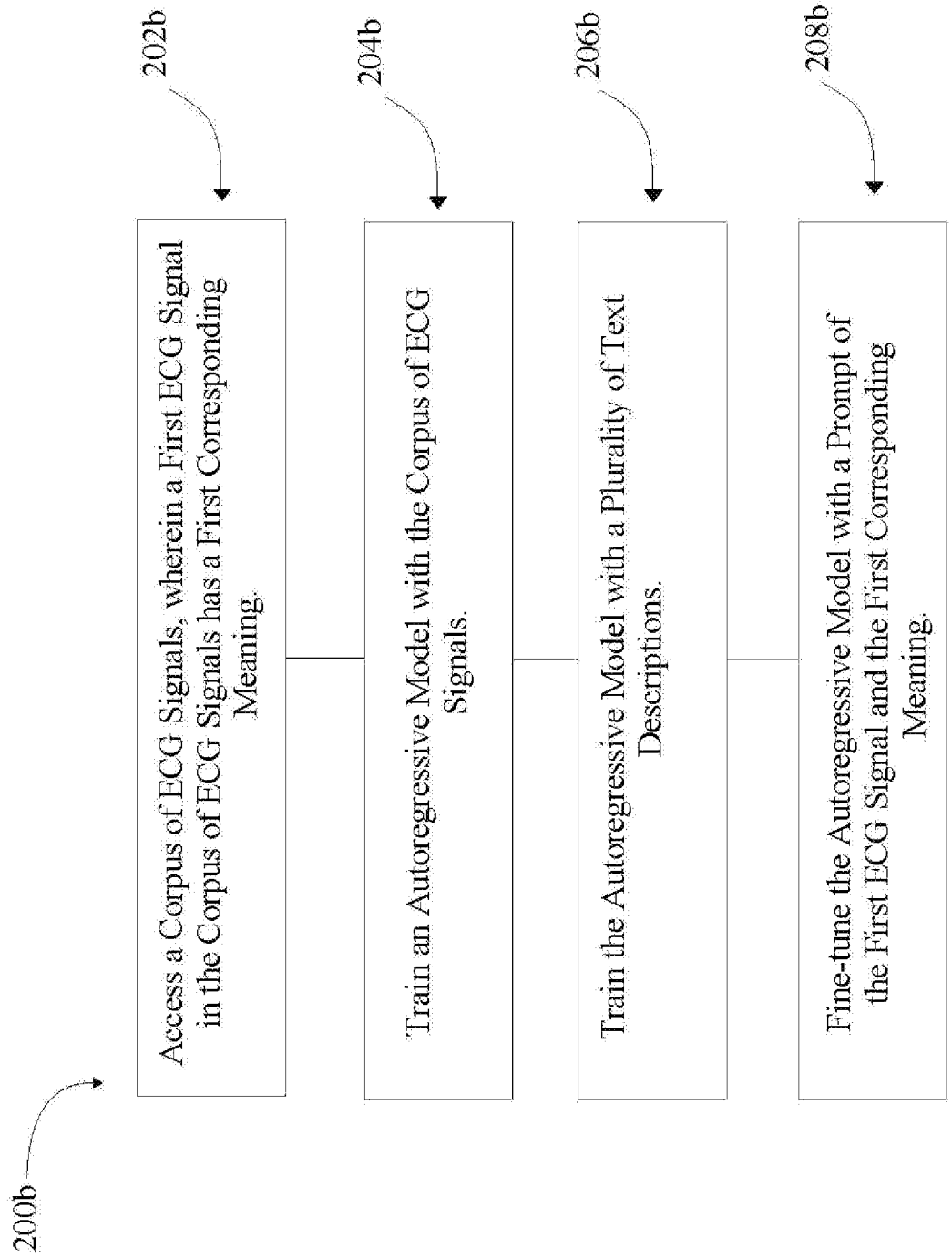

FIG. 2B illustrates a simplified diagram of a method 200b for training a system capable of generating an output based on an ECG device, such as the ECG device 102, in accordance with certain embodiments of the present disclosure. According to some embodiments consistent with FIG. 1, method 200b may be performed by a computer processor, such as processor 112 based on instructions and/or data stored in a memory, such as memory 116. In comparison to method 200a, method 200b describes embodiments in which input data for the AR model includes an ECG signal (e.g., raw or normalized ECG data that has not been transformed or into a lower dimensionality representation) rather than (or in addition to) a representation produced by a quantizing model. At process 202b, a corpus of ECG signals is accessed. At least one ECG signal in the corpus of ECG signals may have a corresponding meaning, thus forming a (ECG signal, corresponding meaning) pair. For example, a first ECG signal may have a first corresponding meaning, e.g., a first corresponding categorical value of a certain disease conditions (e.g., CHD representing congenital heart disease), and/or a first corresponding sequence (e.g. a sentence such as "the patient may have congenital heart disease"). In some embodiments, the corpus of ECG signals and the corresponding meaning may be accessed by the database, such as database 104. In some embodiments, the ECG signal may be accessed by one or more ECG devices 101-103 directly. In some embodiments, additional processes need to be performed to access the corpus of ECG signals, as described with reference to FIG. 3.

At process 204b, and with reference to FIG. 2B, an AR model, such as the autoregressive model 144, is trained with the corpus of ECG signals. After training, the AR model may represent any ECG signal as a continuous representation of that ECG signal, e.g., a fixed set of learned vectors. For example, the first ECG signal may be represented as a first continuous representation of the first ECG signal. Since an ECG signal (e.g., the raw data) may be represented as a set of integers within a definite numeric range, each signal itself among the corpus of ECG signals may be treated as a fixed set of vectors. Hence the corpus of ECG signals as a whole may be treated as a group of continuous representation of ECG signals. In some embodiments, the raw data of the corpus of ECG signals may be normalized. The process may be similar to some or all the process 208a described above. At a process 206b, the AR model, such as the autoregressive model 144, is trained with a plurality of text descriptions. The parameters of the AR model are updated in this stage. In some embodiments, the AR model is trained with both the group of continuous representations of ECG signals and the plurality of text descriptions. The process may be similar to some or all the process 210a described above.

At process 208b, and with reference to FIG. 2B, the AR model is fine-tuned with a prompt including the continuous representation of the first ECG signal and the first corresponding meaning. The fine-tuned autoregressive model can generate an output normally detectable by analyzing an ECHO image. The parameters of the AR model are updated in this stage. The fine-tuned AR model may generate an output, such as output 190, which is normally detectable by analyzing an ECHO image. For example, the AR model may be added to a classification head that converts the continuous representation of the first ECG signal to the output. The process may be similar to some or all the process 212a described above.

Figure 2C:
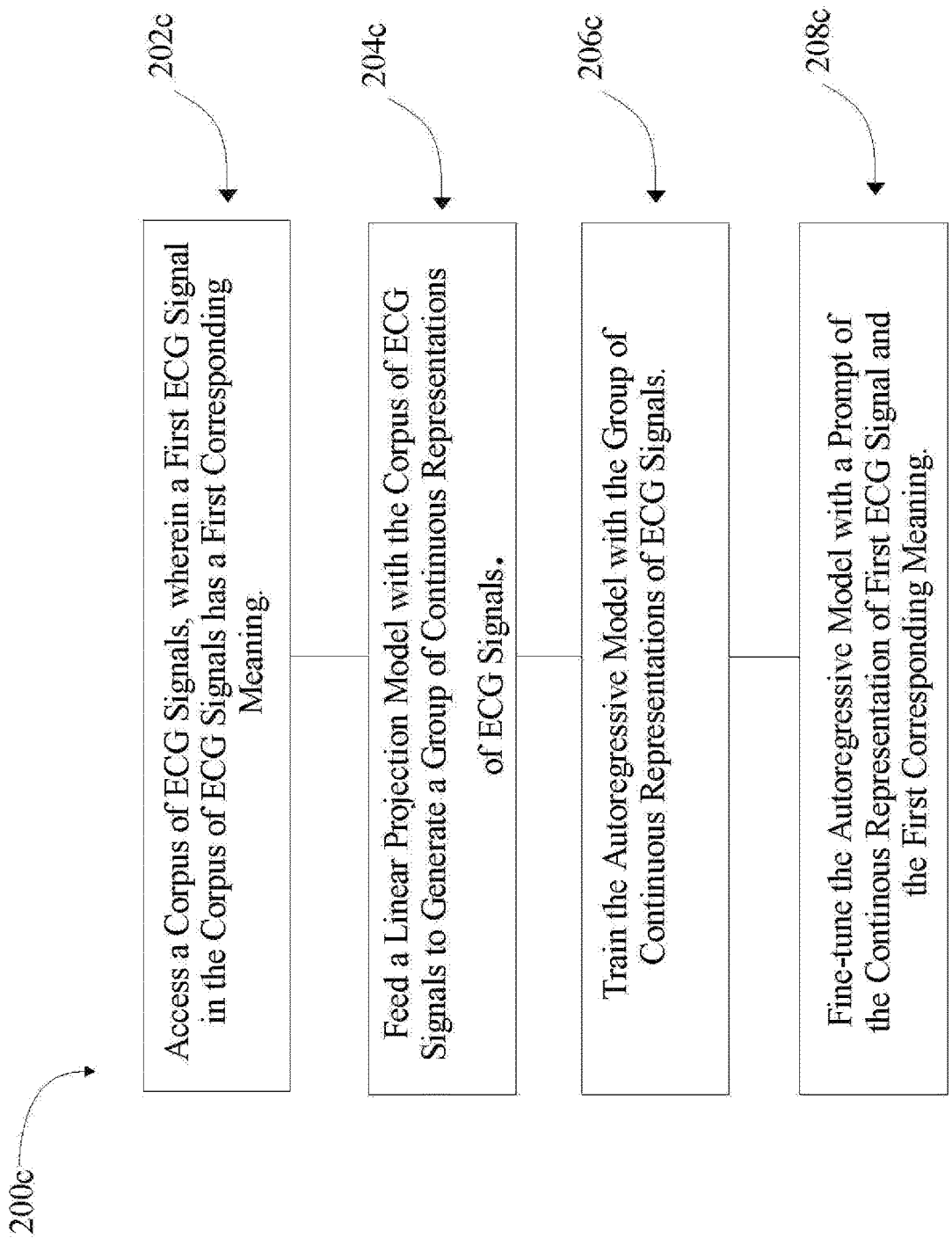

FIG. 2C illustrates a simplified diagram of a method 200c for training a system capable of generating an output based on an ECG device, such as the ECG device 102, in accordance with certain embodiments of the present disclosure. According to some embodiments consistent with FIG. 1, method 200c may be performed by a computer processor, such as processor 120 based on instructions and/or data stored in a memory, such as memory 130. Similar to method 200a, method 200c describes embodiments in which input data for the AR model includes a representation of ECG signal produced by a linear projection model.

At process 202c, and with reference to FIG. 2C, a corpus of ECG signals is accessed. At least one ECG signal in the corpus of ECG signals may have a corresponding meaning, thus forming a (ECG signal, corresponding meaning) pair. For example, a first ECG signal may have a first corresponding meaning, e.g., a first corresponding categorical value of a certain disease conditions (e.g., CHD representing congenital heart disease), and/or a first corresponding sequence (e.g., a sentence such as "the patient may have congenital heart disease"). In some embodiments, the corpus of ECG signals and the corresponding meaning may be accessed by the database, such as database 104. In some embodiments, the ECG signal may be accessed by one or more ECG devices 101-103 directly. In some embodiments, additional processes need to be performed to access the corpus of ECG signals, as described with reference to FIG. 3.

At process 204c, and with reference to FIG. 2C, a linear projection model, such as the liner projection model 154 is fed with the corpus of ECG signals as an input, to generate a group of continuous representation of ECG signals. After training, the linear projection model may represent any ECG signal as a continuous representation of that ECG signal, e.g., a fixed set of learned vectors. For example, the first ECG signals may be represented as a first continuous representation of the first ECG signal. Similar process may be repeated for other ECG signals in the corpus to derive the group of continuous representation of ECG signals. As discussed above, the linear projection (e.g., factor analysis, principal component analysis) may be used to compress the training data by reducing the data from a high dimension to a lower dimension. For example, the linear projection model 154 may be used to compress the corpus of ECG signals to the group of continuous representation of ECG signals by reducing a dimension of the corpus of ECG signal to a lower dimension. The group of continuous representations of ECG signals may be used to reduce the computational overhead of the downstream tasks. For example, the group of continuous representations may be used as the training data for an autoregressive model to reduce the computational overhead.

At process 206c, and with reference to FIG. 2C, an AR model, such as the autoregressive model 144, may be trained with the group of continuous representations of ECG signals. After training, the AR model may represent any ECG signal as a continuous representation of that ECG signal, e.g., a fixed set of learned vectors. For example, the first continuous representation of the first ECG signal may be represented as a second continuous representation of the first ECG signal. The process may be similar to some or all the process 208a described above. At a process 208c, the AR model, such as the autoregressive model 144, may be trained with a plurality of text descriptions. The parameters of the AR model are updated in the stage. In some embodiments, the AR model may be trained with both the group of continuous representations of ECG signals and the plurality of text descriptions. The process may be similar to some or all the process 210a described above. At process 210c, the AR model may be fine-tuned with a prompt including the first continuous representation of the first ECG signal and the first corresponding meaning. The fine-tuned autoregressive model can generate an output normally detectable by analyzing an ECHO image. The parameters of the AR model are updated in the stage. The fine-tuned AR model may generate an output, such as output 190, which may be normally detectable by analyzing an ECHO image. For example, the AR model may add a classification head that converts the continuous representation of the first ECG signal to the output. The process may be similar to some or all the process 212a described above.

Figure 2D:
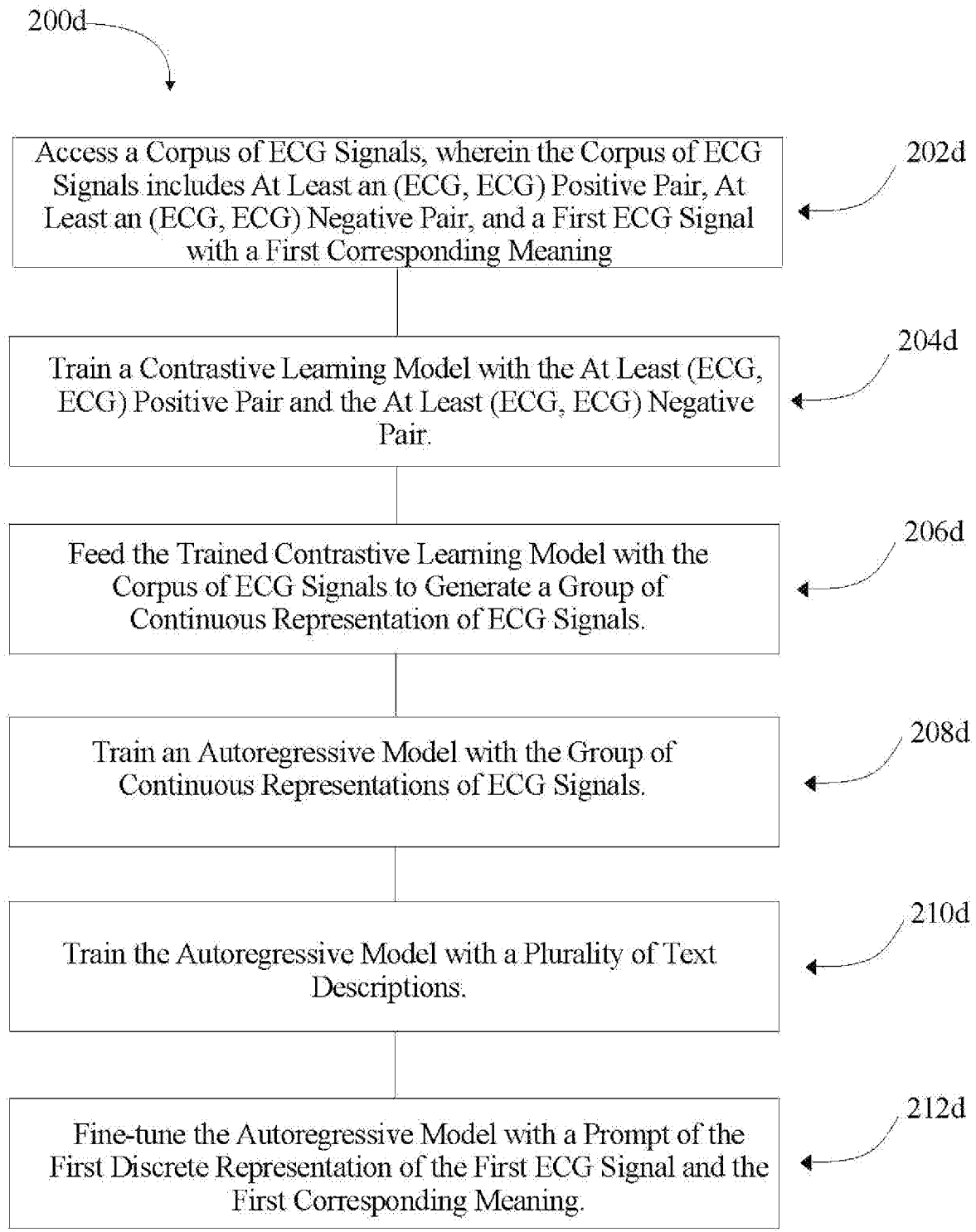

FIG. 2D illustrates a simplified diagram of a method 200d for training a system capable of generating an output based on an ECG device, such as the ECG device 102, in accordance with certain embodiments of the present disclosure. According to some embodiments consistent with FIG. 1, method 200d may be performed by a computer processor, such as processor 120 based on instructions and/or data stored in a memory, such as memory 130. In comparison to methods 200a-c, method 200d describes embodiments in which input data for the AR model includes a representation produced by a contrastive learning model rather than (or in addition to) a representation produced by a quantizing model, e.g., method 200a, raw or normalized ECG data that has not been transformed or into a lower dimensionality representation, e.g., method 200b, and/or a representation produced by a linear projection model, e.g., 200d.

At process 202d, and with reference to FIG. 2D, a corpus of ECG signals may be accessed. At least one ECG signal in the corpus of ECG signals may have a corresponding meaning, thus forming a (ECG signal, corresponding meaning) pair. For example, a first ECG signal may have a first corresponding meaning, e.g., a first corresponding categorical value of a certain disease conditions (e.g., CHD representing congenital heart disease), and/or a first corresponding sequence (e.g., a sentence such as "the patient may have congenital heart disease"). The corpus of ECG signals may form at least an (ECG, ECG) positive pair and at least an (ECG, ECG) negative pair. In some embodiments, the (ECG, ECG) positive pair may be derived by pairing two ECG signals from the same patient, and the (ECG, ECG) negative pair may be derived by pairing two ECG signals from different patients. For example, the first ECG signal and a second signal are derived from patient A, thus forming an (ECG, ECG) positive pair. A third ECG signal may be derived from patient B, and forms an (ECG, ECG) negative pair with the second signal. In some embodiments, the corpus of ECG signals, the corresponding meaning, the (ECG, ECG) positive pair, and the (ECG, ECG) negative pair may be accessed by the database, such as database 104. In some embodiments, the ECG signal may be accessed by one or more ECG devices 101-103 directly. In some embodiments, additional processes need to be performed to access the ECG signal, as described with reference to FIG. 3.

At process 204*d*, and with reference to FIG. 2D, a contrastive learning model, such as the contrastive model 146, may be trained with at least the (ECG, ECG) positive pair and at least the (ECG, ECG) negative pair. In some embodiments, the contrastive learning model may be an encoder network. The encoder network learns to encode the input time series data into a fixed-length vector (e.g., embedding), which captures the salient features of the data that are relevant for the downstream task (e.g., prediction made by an AR model). Specifically, within the unified framework of an energy-based model (EBM), the contrastive model may be trained to produce low energy for the first ECG signal and the second ECG signal since the first and the second ECG signals are derived from the same patient A In some embodiments, the ECG signals from the same patient are tugged closer. Meanwhile, the contrastive model may be trained to produce high energy for the first ECG signal and the third ECG signal since the first and the third ECG signals are derived from different patients (e.g., patient A and patient B). Similarly, the contrastive model may further be trained to produce high energy for the second ECG signal and the third ECG signal.

Still referring to FIG. 2D, processor 112 may be configured to generate Contrastive VIsual Representation Learning from Text (ConVIRT), a framework for learning visual representations by exploiting the naturally occurring pairing of images and textual data. ConVIRT improves visual representations by maximizing the agreement between true image-text pairs versus random pairs via a bidirectional contrastive objective between the image and text modalities. We apply ConVIRT to the pretraining of medical image encoders and show that it leads to higher-quality in-domain image representations that capture the subtlety of visual features required for medical image understanding tasks. Compared to existing methods, ConVIRT has the advantages of utilizing the paired text data in a way agnostic to the medical specialty and requiring no additional expert input. This allows us to evaluate ConVIRT by transferring pre-trained encoder weights to 4 different medical image classification tasks covering 2 medical specialties. We find that the resulting models outperform all baseline initialization approaches, including the widely used ImageNet pretraining and strong baselines that also utilize the paired text data. It further improves upon popular image-only unsupervised learning methods such as SimCLR and MoCo v2. Most notably, in all 4 classification tasks, ConVIRT requires only 10% as much labeled training data as an ImageNet initialized counterpart to achieve better or comparable performance. We further evaluate ConVIRT on two new zero-shot retrieval tasks, an image-image and a text-image retrieval task, and also find it superior to all baselines.

Continuing reference to FIG. 2D, a representation learning setting may be defined including paired input $(x_v, x_u)$ where $x_v$ represents one or a group of images, and $x_u$ represents a text sequence which de-scribes the imaging information in xv. Processor 112 may be configured to learn a parameterized image encoder function $f_v$, which maps an image to a fixed-dimensional vector. Processor 112 may transfer the learned image encoder function $f_v$ into downstream tasks, such as classification or image retrieval. Encoder may be modeled as function $f_v$, as a convolutional neural network (CNN). The method converts each input image $x_v$ and text $x_u$ into d-dimensional vector representations v and u respectively, following a similar processing pipeline. For each input image $x_v$, the method may start by drawing a random view $\tilde{x}_v$ from $x_v$ with a sampled transformation function $t_v \sim T$, where T represents a family of stochastic image transformation functions described in the disclosure. Next, the encoder function $f_v$ transforms $\tilde{x}_v$ into a fixed-dimensional vector $h_v$, followed by a non-linear projection $g_v$ which further transforms $h_v$ into vector v:

$$v=g_v(f_v(\tilde{x}_v)),$$

Where $v \in R^d$. Similarly, for each text input $x_u$ from it following a sampling function $t_u$, and then a text representation u with: $u=g_u(f_u(u))$, where $f_u$ is a text encoder, $g_u$ a projection, and $u \in R^d$. The projection functions $g_v$ and $g_u$ project representations for both modalities from their encoder space to the same d-dimensional space for contrastive learning. At training time, sample a minibatch of N input pairs $(x_v, u)$ from training data, and calculate their representation pairs (v, u). We use $(v_i, x_i)$ to denote the i-th pair. The training objective of ConVIRT involves two loss functions. The first loss function is an image-to-text contrastive loss for the i-th pair:

$$l_i^{(u \to v)} = -\log \frac{\exp\left(\frac{v_i, u_i}{\tau}\right)}{\sum_{k=1}^{N} \exp\left(\frac{u_i, v_k}{\tau}\right)}$$

The final training loss is then computed as a weighted combination of the two losses averaged over all positive image-text pairs in each minibatch:

$$L = \frac{1}{N} \sum_{i=1}^{N} \left(\lambda l_i^{(u \to v)} + (1-\lambda) l_i^{(u \to v)}\right)$$

Where $\lambda \in [0,1]$ is a scalar weight.

For the image encoder $f_v$, ResNet50 architecture may be used for all experiments, as it is the architecture of choice for much medical imaging work and may be shown to achieve competitive performance. For the text encoder $f_u$, a BERT encoder may be used followed by a max-pooling layer over all output vectors. The encoder may be initialized using ClinicalBERT weights pretrained on the MIMIC clinical notes. At training time the encoder may adapt to the contrastive task by freezing the embeddings and the first 6 transformer layers of this BERT encoder and fine-tuning the last 6 layers.

For the image transformation family T where ty may be sampled from, we use sequential applications of five random transformations: cropping, horizontal flipping, affine transformation, color jittering and Gaussian blur. For the text transformation function tu, we apply a simple uniform sampling of a sentence from the input document xu (i.e., $\tilde{x}_u$ is a randomly sampled sentence from $x_u$ for each minibatch). We did not use a more aggressive transformation mainly because sampling at the sentence level helps preserve the semantic meaning of the sampled spans.

An alternative method to using the sampled view $\tilde{x}_v$ from $x_v$ as input to the encoder may be to directly use $x_v$ or to fuse all images for each study in the case of multiple available $x_v$ instances (e.g., images from multiple angles). Using sampled view $\tilde{x}_v$ may lead to better pretraining results. Paired image-text data $(x_v, x_u)$ naturally exists for many medical domains. Medical experts such as radiologists produce textual descriptions of images as part of their routine workflow.

With reference to FIG. 2D, ConVIRT may be pretrained using two separate image encoders using two separate image-text datasets including Chest image encoder, Bone image encoder, and the like. The pretrained image encoder by be evaluated using at least three medical imagining tasks including image classification, zero-shot image-image retrieval and zero-shot text-image retrieval. The ConVIRT may be compared against standard or competitive initialization methods such as Random Init, ImageNet Init, Caption-LSTM, Caption-Transformers, Contrastive-Binary-Loss, and the like.

At process 206d, and with reference to FIG. 2D, the trained contrastive model is fed with the corpus of ECG signals to generate a group of continuous representation of ECG signals. The trained contrastive model may represent any ECG signals as a continuous representation of that ECG signal. For example, the trained contrastive model may transform the first ECG signals into a first continuous representation of the first ECG signal. Similar process may be repeated for other ECG signals in the corpus to derive the group of continuous representation of ECG signals.

At process 208d, and with reference to FIG. 2D, an AR model, such as the autoregressive model 144, is trained with the group of continuous representations of ECG signals. After training, the AR model may represent any ECG signal as a continuous representation of that ECG signal, e.g., a fixed set of learned vectors. For example, the first continuous representation of the first ECG signal may be represented as a second continuous representation of the first ECG signal. The process may be similar to some or all the process 208a described above.

As described above, and with reference to FIG. 2D, the amount of (ECG, ECG) positive and/or pairs may be relatively scarce and/or too expensive to collect. This may be due to the requirement that the two ECG signals should be done within a time window (say within one month). Contrastive learning is suitable for this scenario because it can be used to learn embeddings from relatively small amounts of data. By using contrastive learning, the AR model can learn representations that are more data-efficient and better able to generalize to new, unseen data.

Further, and with reference to FIG. 2D, the performance of the AR model may be improved by using contrastive learning to learn the embedding of the input data, especially when high-dimensional and complex time series data is involved (e.g., the corpus of ECG signals). The learned embedding may capture the salient and informative feature of the data, making it easier for the AR model to make more accurate and reliable prediction. By the same token, contrastive learning can help to make the AR model more robust to noise and variability in the input data. By learning embeddings that capture the underlying structure of the data, the AR model can better handle variations in the data due to noise, measurement errors, or other sources of variability. Meanwhile, contrastive learning can be used to learn embeddings that are interpretable and can provide insights into the underlying structure of the data. For example, contrastive learning may help the AR model to understand the factors in the ECG signals that drives the prediction (e.g., predicting categorical values of certain disease conditions, sentences describing the disease conditions).

At process 210d, and with reference to FIG. 2D, the AR model, such as the autoregressive model 144, may be trained with a plurality of text descriptions. The parameters of the AR model may be updated in this stage. In some embodiments, the AR model may be trained with both the group of continuous representations of ECG signals and the plurality of text descriptions. The process may be similar to some or all the process 210a described above.

At process 212d, and with reference to FIG. 2D, the AR model may be fine-tuned with a prompt including the first continuous representation of the first ECG signal and the first corresponding meaning. The fine-tuned autoregressive model can generate an output normally detectable by analyzing an ECHO image. The parameters of the AR model are updated in this stage. The fine-tuned AR model may generate an output, such as output 190, which is normally detectable by analyzing an ECHO image. For example, the AR model may be added a classification head that converts the continuous representation of the first ECG signal to the output. The process may be similar to some or all the process 212a described above.

Figure 3:
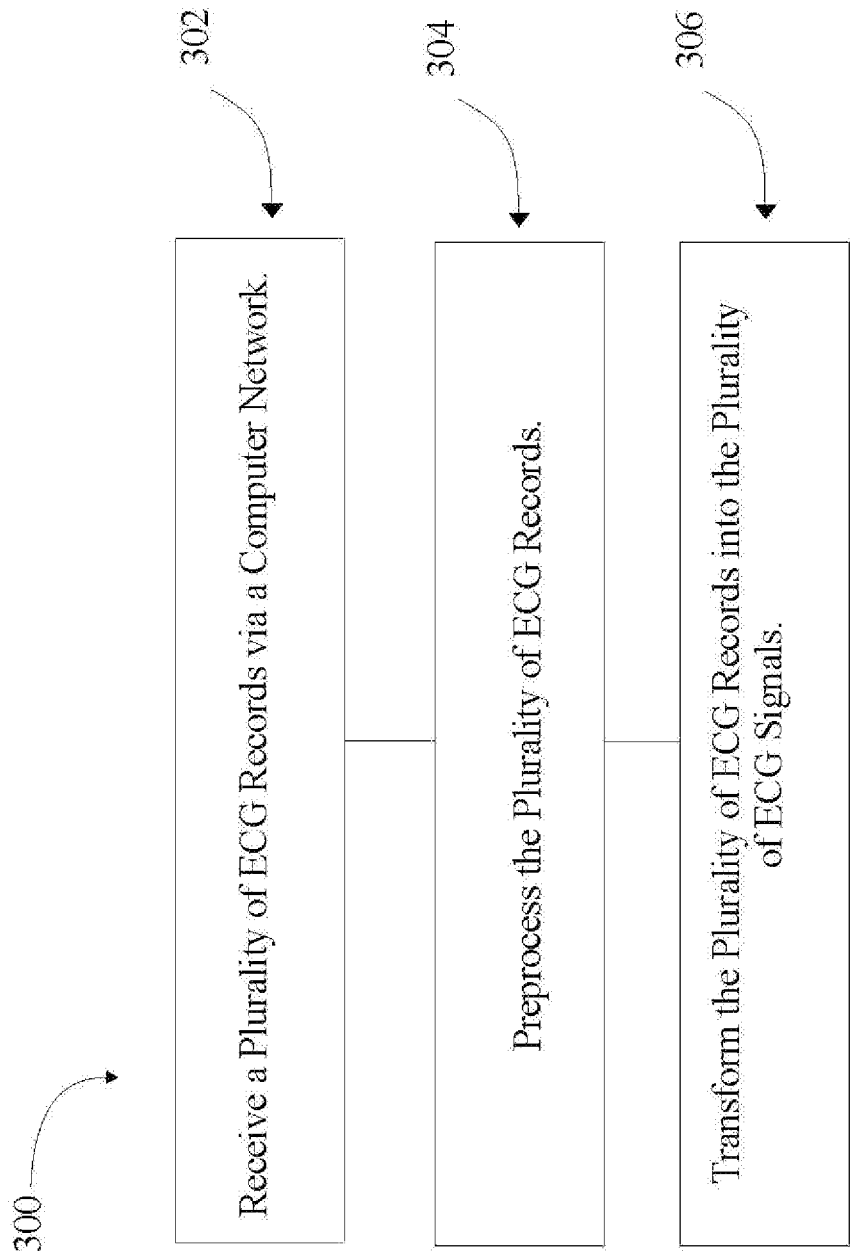
FIG. 3 is diagrammatic representation of a method for accessing a plurality of ECG signal in accordance with certain embodiments of the present disclosure.

FIG. 3 illustrates a simplified diagram of a method 300 for accessing a plurality of ECG signal in accordance with certain embodiments of the present disclosure. According to some embodiments consistent with FIG. 3, method 300 may be performed by a computer processor, such as processor 112 based on instructions and/or data stored in a memory, such as memory 116.

At process 302, and with reference to FIG. 3, the processor receives one or more ECG records 111-113, from a computer network, such as the computer network 124. The one or more ECG records 111-113 may be generated by one or more ECG devices, such as the ECG devices 111-113. The ECG record is an electrogram of the heart which is a graph of voltage versus time of the electrical activity of the heart using electrodes placed on the skin of the patient. The ECG record can be transmitted and received in a variety of image formats (e.g., JPEG, PNG, TIFF image). A format conversion engine may be selected to transform the ECG record into a uniform image independent of the format of the received ECG record format. In this manner, flexibility is provided to handle a wide variety of format types of received digital ECG record.

At process 304, and with reference to FIG. 3, the processor preprocesses the ECG record. Various pre-processing steps may be performed. These pre-processing steps can include cropping and/or padding the ECG record to fit a predetermined aspect ratio, scaling the dimensions of ECG record to fit a predetermined size, segmenting the ECG record into a plurality of segments, or the like.

At process 306, and with reference to FIG. 3, the processor transforms the ECG record into an ECG signal. In some embodiments, the ECG signal may be normalized so that the values of each element in the vectors may fall within a range of integers.

Figure 4:
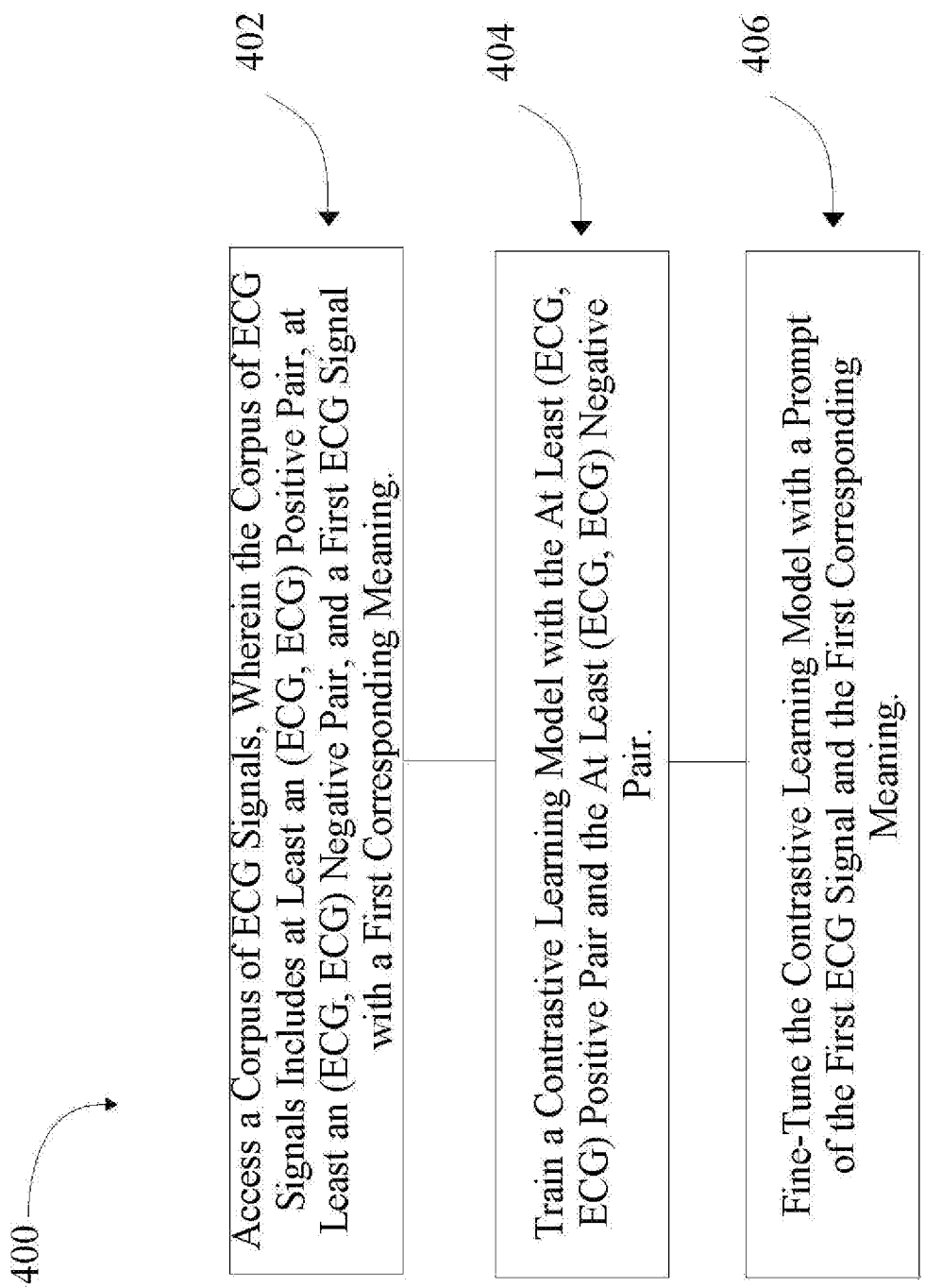
FIG. 4 is a diagrammatic representation of a method for training a system capable of generating an output based on an ECG device, in accordance with certain embodiments of the present disclosure.

FIG. 4 illustrates a simplified diagram of a method 400 for training a system capable of generating an output based on an ECG device, such as the ECG device 102, in accordance with certain embodiments of the present disclosure. According to some embodiments consistent with FIG. 4, method 400 may be performed by a computer processor, such as processor 120 based on instructions and/or data stored in a memory, such as memory 130. The trained system may take (ECG, ECG) positive and (ECG, ECG) negative pairs as the input and generate a scalar value normally derived from an ECHO. The scalar value may be used for disease diagnosis. The scalar value may include categorical value of a certain disease conditions (e.g., CHD representing congenital heart disease). In comparison to the methods described in FIGS. 2A-D, method 400 describes embodiments in which input data may be fed to a contrastive learning model, rather than an AR model.

At process 402, and with reference to FIG. 4, a corpus of ECG signals may be accessed. At least one ECG signal in the corpus of ECG signals may have a corresponding meaning, thus forming a (ECG signal, corresponding meaning) pair. For example, a first ECG signal may have a first corresponding meaning, e.g., a corresponding categorical value of a certain disease conditions (e.g., CHD).

With reference to FIG. 4, The corpus of ECG signals may form at least an (ECG, ECG) positive pair and an (ECG, ECG) negative pair. In some embodiments, the (ECG, ECG) positive pair may be derived by pairing two ECG signals from the same patient, and the (ECG, ECG) negative pair may be derived by pairing two ECG signals from different patients. For example, the first ECG signal and a second signal are derived from patient A, thus forming an (ECG, ECG) positive pair. A third ECG signal is derived from patient B, and forms an (ECG, ECG) negative pair with the second signal.

With reference to FIG. 4, In some embodiments, the corpus of ECG signals, the corresponding meaning pair, the (ECG, ECG) positive pair and the (ECG, ECG) negative pair may be accessed by the database, such as database 104. In some embodiments, the ECG signal may be accessed by one or more ECG devices 101-103 directly. In some embodiments, additional processes need to be performed to access the ECG signal, as described with reference to FIG. 3.

At process 404, and with reference to FIG. 4, a contrastive learning model, such as the contrastive model, may be trained with at least the (ECG, ECG) positive pair and at least the (ECG, ECG) negative pair. The trained contrastive model may represent any ECG signals as a continuous representation of that ECG signal. For example, the trained contrastive model may transform the first ECG signals into a continuous representation of the first ECG signal. The process may be similar to some or all the process 204c described above.

At process 406, and with reference to FIG. 4 the contrastive model may be fine-tuned with a prompt including the ECG signal and the corresponding meaning. The parameters of the contrastive model are updated in this stage. For example, a prompt of the first ECG signal and the first corresponding meaning is used to fine-tune the contrastive model. The fine-tuned contrastive model may generate an output which is normally detectable by analyzing an ECHO image.

With reference to FIG. 4, the ECG signals and their corresponding meaning may be used to fine-tune the contrastive model to achieve the desired output and performance. For example, the first ECG signal and its corresponding meaning (e.g., CHD) may be used to fine-tune the contrastive model. In some embodiments, the output may be a scalar value. The scalar value may include classification code, categorical value, and numeric value describing disease conditions, then the autoregressive model may be fine-tuned with a plurality of fixed sets of vectors and the corresponding scalar value pairs. Such scalar value is representative of information normally detectable from an echocardiogram. The doctors may use such scalar value for diagnosis. In some embodiments, the fine-tuned contrastive model may be executed with a particular ECG signal as an input to generate an output which is normally detectable by analyzing an ECHO image.

Figure 5:
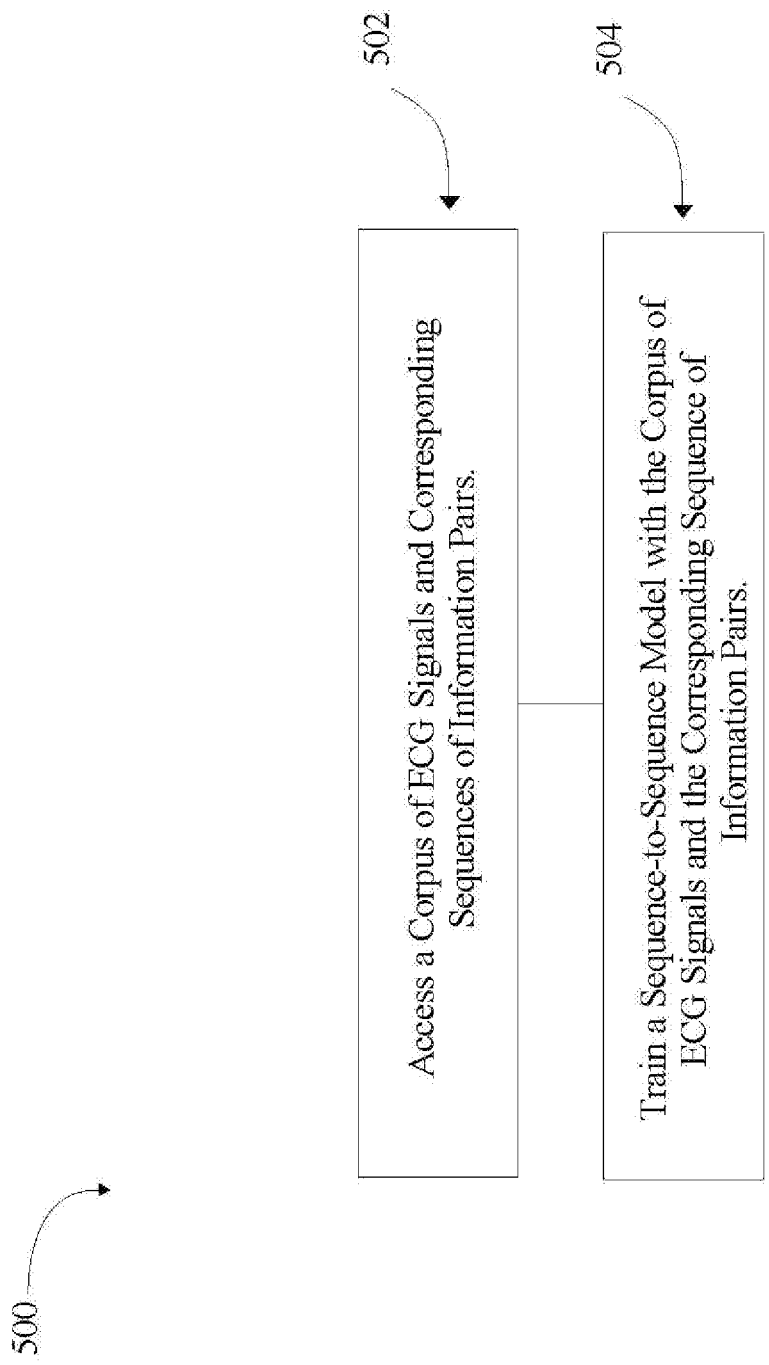
FIG. 5 is a diagrammatic representation of a method for training a system capable of generating a sequence of information based on an ECG device, in accordance with certain embodiments of the present disclosure.

FIG. 5 illustrates a simplified diagram of a method 500 for training a system capable of generating a sequence of information based on an ECG device, such as the ECG device 102, in accordance with certain embodiments of the present disclosure. According to some embodiments consistent with FIG. 5, method 500 may be performed by a computer processor, such as processor 120 based on instructions and/or data stored in a memory, such as memory 116. The trained system may take (ECG, corresponding meaning) pairs as the input and generate a sequence normally derived from an ECHO. The scalar value may be used for disease diagnosis. A sequence may include a sentence such as "the patient may have congenital heart disease". In comparison to the methods described in FIGS. 2A-D and FIG. 4, method 500 describes embodiments in which input data is fed to a sequence-to-sequence model, rather than an AR model or a contrastive learning model.

At process 502, and with reference to FIG. 5, a corpus of ECG signals and corresponding sequences of information pairs may be accessed. The sequence of information may include a sentence describing a disease condition, a 1-D waveform when the echocardiogram is operated under the motion mode (M-mode). For example, a first ECG signal may have a corresponding sequence of information (e.g., a sentence such as "the patient may have congenital heart disease"). In some embodiments, the plurality of ECG signal and corresponding meaning pairs may be accessed from a data base, such as the database 104. In some embodiments, additional processes need to be performed to access the corpus of ECG signals, as described with reference to FIG. 3.

At process 504, and with reference to FIG. 5, a sequence-to-sequence model, such as the sequence-to-sequence model, may be trained with the corpus of ECG signals and corresponding sequence of information pairs. The parameters of the sequence-to-sequence model are updated in supervised way in this stage. The trained sequence-to-sequence model may generate an output, such as output 190, which is normally detectable by analyzing an ECHO. In some embodiments, the sequence-to-sequence model may include an encoder-decoder pair. In some embodiments, the output may be a sequence of information. The sequence of information may include a sentence describing a disease condition, a 1-D waveform when the echocardiogram is operated under the motion mode (M-mode), etc. Such sequence of information is representative of information normally detectable from an echocardiogram. The doctors may use such sequence of information for diagnosis. In some embodiments, the system may be executed with a particular ECG signal as an input to generate an output, which is normally detectable by analyzing an ECHO image. In some embodiments, the trained sequence-to-sequence model may represent any ECG signals as a continuous representation of that ECG signal. For example, the trained sequence-to-sequence model may represent the first ECG signals as a continuous representation of the first ECG signal.

Figure 6:
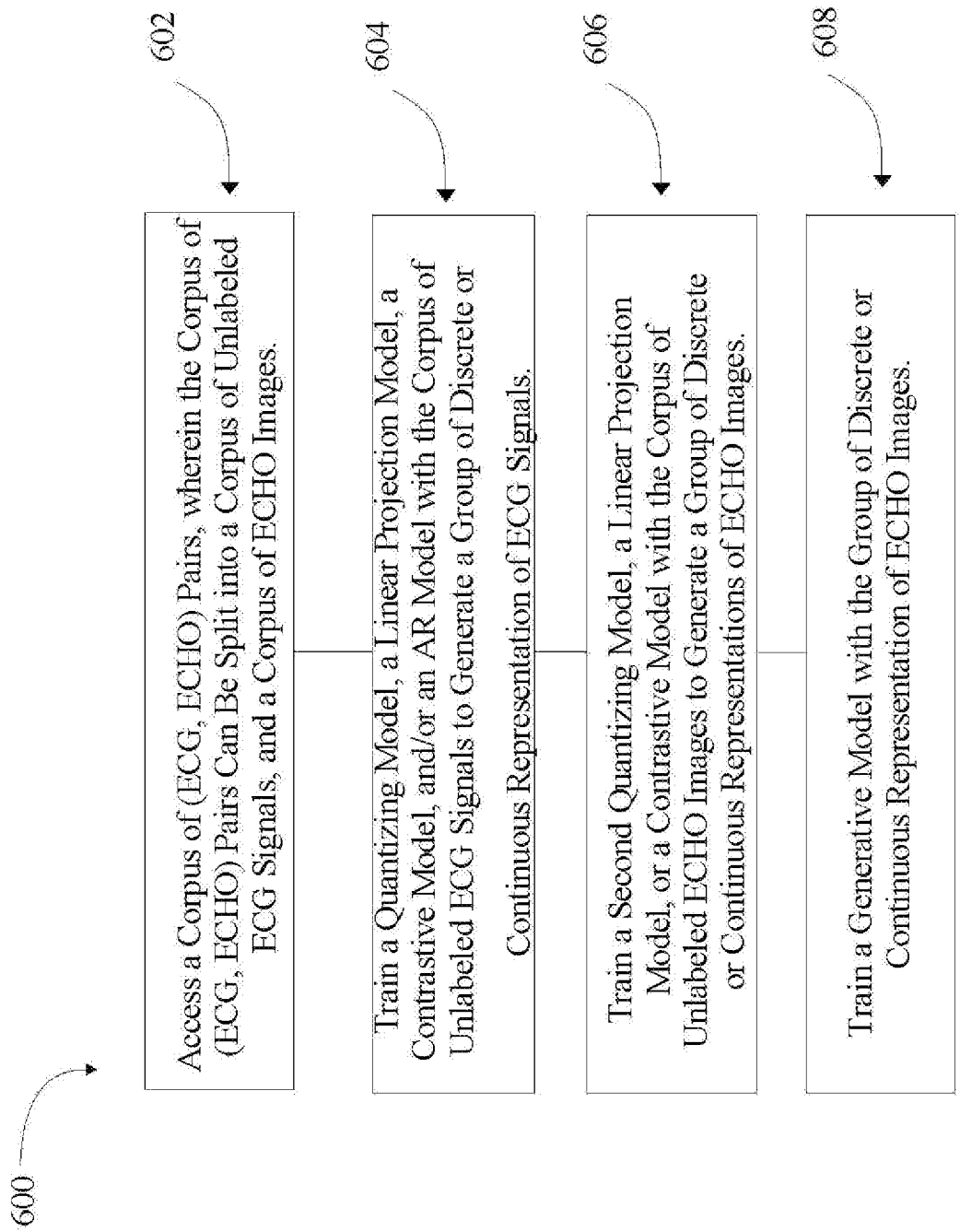
FIG. 6 is a diagrammatic representation of a method for training a system capable of generating an output based on an ECG, in accordance with certain embodiments of the present disclosure.

FIG. 6 illustrates a simplified diagram of method 600 for training a system capable of generating an output based on an ECG, such as the ECG 102, in accordance with certain embodiments of the present disclosure. According to some embodiments consistent with FIG. 6, method 600 may be performed by a computer processor, such as processor 160 based on instructions and/or data stored in a memory, such as memory 150. Method 600 may include training three sets of models, and the models may include some or all of the models described above. The first set of models may be trained with ECG signals as input, and it may include a quantizing model, a linear projection model, a contrastive model and/or an AR model with the corpus of ECG signals. The second set of models may be trained with ECHO as input, and it may include a quantizing model, a linear projection model, or a contrastive model. The benefits for training the set of models are the same as described above and won't be repeated herein for brevity. The third set of models may be trained with ECHO images as input, and it may include a diffusion model. The trained diffusion model may take the output of the first and the second set of models as input, to generate the 2D/3D ECHO and/or a sequence of 2D/3D ECHO. For example, the trained system may take a target ECG signal and a reference ECHO as the input and generate a 2D/3D ECHO and/or a sequence of 2D/3D ECHO which may be used for disease diagnosis. The target ECG signal may manipulate the reference ECHO to derive the 2D/3D ECHO as the output. The detailed process is to be described with FIGS. 7-8 below.

At process 602, and with reference to FIG. 6, a corpus of (ECG, ECHO) pairs may be accessed. In some embodiments, an (ECG, ECHO) pair may be derived by pairing an ECG signal and an ECHO image from the same patient. For example, a reference ECG signal and a reference ECHO image are derived from a healthy people A, thus forming a reference (ECG, ECHO) pair. A target ECG signal and a target ECHO image are derived from a patient B, thus forming a target (ECG, ECHO) pair.

With reference to FIG. 6, Meanwhile, the corpus of (ECG, ECHO) pairs may be split into a corpus of ECG signals, and a corpus of ECHO images. For example, the corpus of ECG signals may include the reference ECG signal and the target ECG signal, and the corpus of ECHO images may include the reference ECHO image and the target ECHO image. In some embodiments, the corpus of ECG signals and/or the corpus of ECHO images may be unlabeled data.

With reference to FIG. 6, in some embodiments, the corpus of (ECG, ECHO) pairs may be accessed by the database, such as database 140. In some embodiments, the ECG signal may be accessed by one or more ECG devices 101-103 directly. In some embodiments, additional processes need to be performed to access the ECG signal, as described with reference to FIG. 3.

At process 604, and with reference to FIG. 6, a quantizing model, a linear projection model, a contrastive model and/or an AR model may be trained with the corpus of ECG signals, to generate a group of discrete or continuous representation of ECG signals. The process 604 may include some or all the processes, e.g., the processes 202a-210a described in FIG. 2A, the process 202c-210c described in FIG. 2C above. In some embodiments, a linear projection model (e.g., factor analysis, principal component analysis) may be used to compress input data (e.g., the corpus of ECG signals) by reducing the data from a high dimension to a lower dimension. The process may include some or all the processes, e.g., the processes 202b-208b described in FIG. 2B above. The trained quantizing model, the linear projection model, the trained contrastive model, and/or the trained AR model may represent any ECG signal as a discrete or continuous representation of that ECG signal. For example, the trained quantizing model and/or the trained AR model may transform a first ECG signal into a discrete representation of the first ECG signal. As the other example, the trained contrastive model and/or the trained AR model may transform the first ECG signal into a continuous representation of the first ECG signal.

At process 606, and with reference to FIG. 6, a second quantizing model, a second linear projection model, or a second contrastive model may be trained with the corpus of unlabeled ECHO images, to generate a group of representations of ECHO images. Since an ECHO image may be represented as a set of integers within a definite numeric range, the process 606 may be similar to some or all the process 202a-210a described in FIG. 2A, the process 202c-210c described in FIG. 2C above. In some embodiments, a linear projection model (e.g., factor analysis, principal component analysis) may be used to compress input data (e.g., the corpus of ECG signals) by reducing the data from a high dimension to a lower dimension. The process may include some or all the processes, e.g., the processes 202b-208b described in FIG. 2B above. The trained second quantizing model, the trained second linear projection model and/or the trained second contrastive model may represent any ECHO image as a discrete or continuous representation of that ECHO image. For example, the trained quantizing model may transform a first ECHO image into a discrete representation of the first ECHO image. As the other example, the trained contrastive model may transform the first ECG signal into a continuous representation of the first ECG signal. The trained second quantizing model and/or the trained second contrastive model may perform similar process for other ECHO images among the corpus of ECHO to derive the group of discrete representations of ECHO images. As an autoencoder, the quantizing model may compress the high-dimension data into a low-dimension data (e.g., a latent representation). The corpus of ECHO images may be compressed into the group of latent representations which may be used to reduce the computational overhead of the downstream tasks. For example, the group of discrete representations may be used as the training data for the AR model and/or a diffusion model to reduce the computational overhead.

At process 608, and with reference to FIG. 6, a generative model, such as the diffusion model 150, may be trained with the group of representations of ECHO images and/or the corpus of ECHO images. The generative model may be trained to output a 2D/3D ECHO image, and/or a sequence of images. Doctors may use such the image for disease diagnosis. The group of representations of ECHO images may be discrete or continuous. For example, the discrete representation of ECHO images may be generated by the trained quantizing model (e.g., VQ-V AE, VQ-GAN). The continuous representation of ECHO images may be generated by the trained contrastive model. In some embodiments, the diffusion model may be trained with the corpus of ECHO images as input.

With reference to FIG. 6, as a type of generative model, diffusion models may be trained by a forward diffusion process and a backward diffusion process. The forward diffusion process incrementally adds noise (e.g., Gaussian noise) to an input and the input would become a latent representation after iterations. The backward diffusion process recovers the original input by incrementally removing the added noise. Once trained, these models can sample from a Gaussian noise and create an image by the recovery process learned during training. Diffusion models have recently surpassed GAN s in their generative quality of images (e.g., in photorealism and fidelity), in addition to having other benefits over GANs such as training stability.

Figure 7:
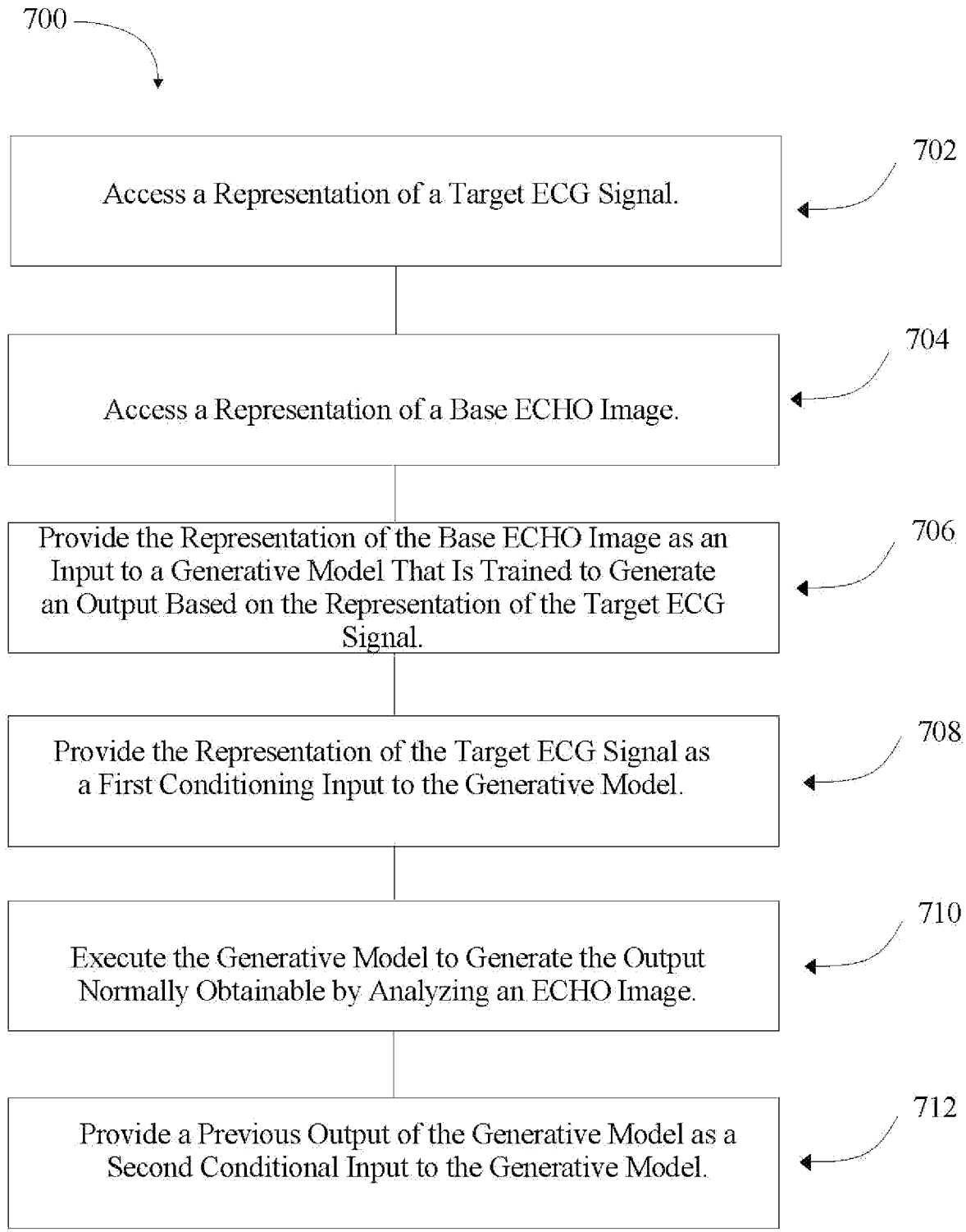
FIG. 7 is a diagrammatic representation of a method for using the system in FIG. 6 to generate an output based on an ECG, in accordance with certain embodiments of the present disclosure.

FIG. 7 illustrates a simplified diagram of a method 700 for using the system in FIG. 6 to generate an output based on an ECG, such as the ECG 102, in accordance with certain embodiments of the present disclosure. According to some embodiments consistent with FIG. 7, method 700 may be performed by a computer processor, such as processor 112 based on instructions and/or data stored in a memory, such as memory 150. Method 700 may include taking a target ECG signal and a reference ECHO as the input to generate a 2D/3D ECHO and/or a sequence of 2D/3D ECHO which may be used for disease diagnosis. The target ECG signal may manipulate the reference ECHO to derive the 2D/3D ECHO and/or a sequence of 2D/3D ECHO as the output. In some embodiments, a cascade of diffusion models may be used to generate photorealistic images at high resolutions. At process 702, a representation of a target ECG signal is accessed. In some embodiments, the target ECG signal may be accessed by the database, such as database 104. In some embodiments, the target ECG signal may be accessed by one or more ECG devices 101-103 directly. In some embodiments, additional processes need to be performed to access the ECG signal, as described with reference to FIG. 3. The processes to be described below will be used to extract information in the target ECG signal. In some embodiments, since an ECG signal may be represented by as a set of integers within a definite numeric range, the representation of the target ECG signal may be the target ECG signal itself (e.g., the normalized raw data). In some embodiments, the representation of the target ECG signal may be discrete, and the discrete representation of the target ECG signal may be derived by performing e.g., the process 604 in FIG. 6.

Continuing to refer to FIG. 7, At process 704, a representation of a base ECHO image is accessed. In some embodiments, the base ECHO image, such as the image 115, may be accessed by the database, such as database 140. In some embodiments, the base ECHO image may be accessed by the ECHO device 104 directly. The base ECHO image may be derived from any people. In some embodiments, the base ECHO image may come from a patient who an ECG test is performed on. In some embodiments, the base ECHO image doesn't reflect any disease condition (e.g., normal, healthy). The base ECHO image may be used as the blackboard to visualize the potential information (e.g., disease conditions) hidden in the target ECG signal. In some embodiments, since an ECHO image may be represented by as a set of integers within a definite numeric range, the representation of the base ECHO image may be the base ECHO image itself (e.g., the normalized raw data). In some embodiments, the representation of the base ECHO image may be discrete, and the discrete representation of the base ECHO image may be derived by performing e.g., the process 606 in FIG. 6. As described above, converting an input (e.g., an ECHO image, an ECG signal) into a discrete representation has proven key for some of the recent progress in computer vision. The latent representation may be used to reduce the computational overhead of the downstream tasks. For example, the discrete representation may be used as input to a generative model to reduce the computational overhead.

Continuing to refer to FIG. 7, at process 706, the representation of the base ECHO image may be provided as an input to a trained generative model. The generative model is trained to generate an output (e.g., an ECHO image) based on the representation of the target ECG signal. Specifically, the generative model may be a diffusion model, such as the diffusion model 150.

In a non-limiting embodiment, and with continuous reference to process 700, All 2D operations, layers, and noise inputs may be replaced by 3D. Structure and formulation of are used as the base and the cosine noise schedule proposed in is adapted. The forward noising process q for a given input image $x_0$ by gradually adding small amounts of Gaussian noise based on the cosine noise schedule in T steps sampled from uniform distribution. The reverse process $p\theta$ is learned by optimizing the model parameters. The main architecture of the proposed method is shown in FIG. 1.

Continuing to refer to FIG. 7 at process 708, the representation of the target ECG signal may be provided as a first conditioning input to the generative model. The generative model may output a 2-D and/or 3D ECHO image. Diffusion model can generate image(s) represented by such a vocabulary of discrete representations either unconditionally or conditioned on text, image, etc. If there is no conditioning input provided, the diffusion model would try to generate an output which is faithful to the input (i.e., trying to duplicate the input as the output). However, the diffusion model may be manipulated by a conditioning input (e.g., a text, a set of vectors). In other words, the conditioning input may be used to manipulate the output of the generative model. In some embodiments, a representation of the target ECG signal may be used as a conditioning input to manipulate the output of the generative model. In other words, the representation of the base ECHO image may be used as the blackboard to visualize the potential information (e.g., disease conditions) hidden in the representation of the target ECG signal. For example, some or all the processes to be described in FIG. 8 may be performed to manipulate the output of the generative model based on the conditioning input.

Continuing to refer to FIG. 7, at process 710, the generative model may be executed to generate an output. The output may be normally obtainable by analyzing an ECHO image. In some embodiments, the output may be a 2-D image, a 3-D image of an ECHO. The generative model may take the representation of the target ECG signal as a conditioning input, and visualize the information (e.g., potential disease conditions) hidden in the target ECG signal on the representation of the base ECHO images (e.g., an ECHO images for a healthy people), thus deriving a new ECHO image. In some embodiments, a cascade of diffusion models, such as a cascade of diffusion models, may be used to generate high-quality ECHO images which further improves the downstream task performance. The cascade of diffusion models accepts a conditioning vector input (e.g., the representation of the target ECG signal) and up-samples the ECHO images in each stage (conditioned on the same text representation) using a diffusion model to generate photorealistic images at high resolutions. For example, a second trained diffusion model may take the output of the generative model as an input, and further take the same representation of the target ECG signal as a conditioning input to generate photorealistic images at high resolutions. At a process 712, a previous output of the generative model is provided as a second conditional input to the generative model. In some embodiments, the previous output is the output generated in the process 710. The previous output and the new output are capable of forming an image sequence (e.g., a proxy for a video) of ECHO images. In some embodiments, the image sequence can depict the development of disease condition continuously.

Figure 8:
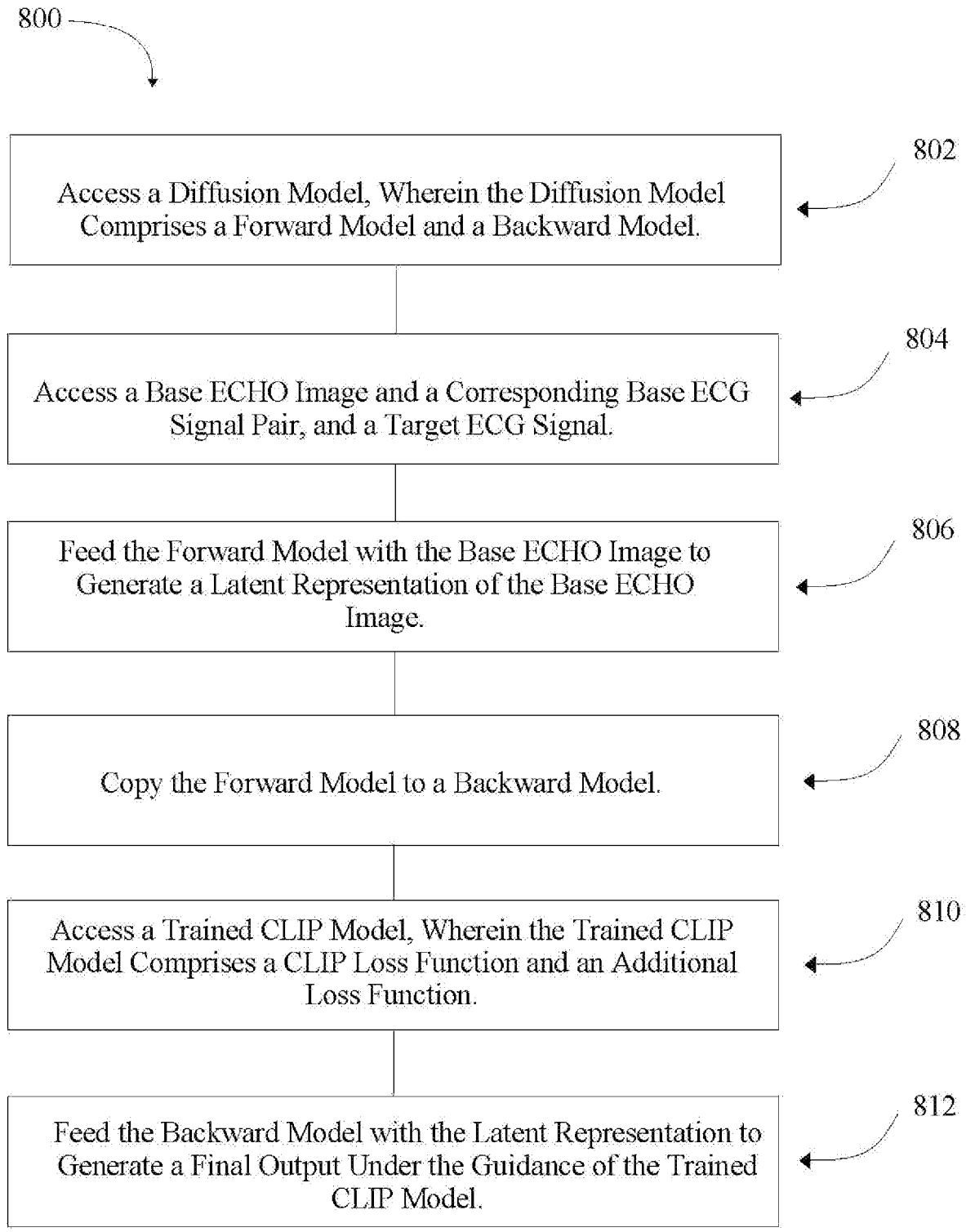
FIG. 8 is a diagrammatic representation of a method for fine-tuning a diffusion model to manipulate the output based on ECG signal, in accordance with certain embodiments of the present disclosure.

FIG. 8 illustrates a simplified diagram of a method 800 for fine-tuning a diffusion model to manipulate the output based on ECG signal, in accordance with certain embodiments of the present disclosure. According to some embodiments consistent with FIG. 8, method 800 may be performed by a computer processor, such as processor 160 based on instructions and/or data stored in a memory, such as memory 150. The method 800 may take a target ECG signal and a reference ECHO as the input to generate a 2D/3D ECHO and/or a sequence of 2D/3D ECHO which may be used for disease diagnosis. The target ECG signal may manipulate the reference ECHO to derive the 2D/3D ECHO and/or a sequence of 2D/3D ECHO as the output. At process 802, a diffusion model, such as the diffusion model 150, is accessed. The diffusion model is trained with the corpus of ECHO images. In some embodiments, the diffusion model 1004 is a denoising diffusion probabilistic model (DDPM). At process 804, a base ECHO image and a corresponding base ECG signal pair, and a target ECG signal are accessed. In some embodiments, the base ECHO image and the base ECG signal pair, and the target ECG signal may be accessed by the database, such as database 104. In some embodiments, additional processes need to be performed to access the corpus of ECG signals, as described with reference to FIG. 3.

Continuing to refer to FIG. 8, In some embodiments, the base ECHO image and the base ECG signal doesn't reflect any disease condition (e.g., normal, healthy). The base ECHO image may be used as the blackboard to visualize the potential information (e.g., disease conditions) hidden in the target ECG signal. In some embodiments, the base ECHO image may be the base ECHO image in FIG. 7. The base ECHO image and the corresponding base ECG signal on the one hand, and the target ECG signal on the other, may come from the same or different people. For example, the base ECHO image and the based ECG signal may come from a healthy people A The target ECHO signal may come from a patient B, or from the people A when s/he ills.

Continuing to refer to FIG. 8, at process 806, a forward model of the diffusion model may be fed with the base ECHO image to generate a latent representation of the base ECHO image. As those skilled in the art would appreciate, the forward process is a fixed Markov chain with Gaussian transition where noise is gradually added, and the latent representation may be a noise distribution.

Continuing to refer to FIG. 8, at process 808, the forward model may be copied to a backward model of the diffusion model. The backward model will be fine-tuned to generate a final output to be described below.

Continuing to refer to FIG. 8, at process 810, a trained CLIP model, such as the CLIP model 152 may be accessed. The CLIP model may include a CLIP loss function and an additional loss function. The CLIP model may be trained to guide the output of the diffusion model by determining the similarity between the output and the target ECG signal. In some embodiments, the CLIP loss function and the additional loss function of the CLIP model may consider some or all the following values as input(s): a base ECHO image and a corresponding base ECG signal pair, and a target ECG signal. The CLIP model may be trained by performing some or all steps described in FIG. 9 below.

Continuing to refer to FIG. 8, in a non-limiting an input image may be first converted to the latent noises through a forward diffusion. In a case using denoising diffusion implicit models (DDIM), latent noises can be inverted nearly perfectly to the original image using a reverse diffusion if the score function for the reverse diffusion is retained the same as that of a forward diffusion model. Diffusion-CLIP may be used to fine-tune the score function in the reverse diffusion process using a CLIP loss that controls the attributes of the generated image based on the text prompts.

Continuing to refer to FIG. 8, with continued reference to process 800, DiffusionCLIP may be used to perform image manipulation both in the trained and unseen domain. DiffusionCLIP may be used to translate the image from an unseen domain into another unseen domain or generate images in an unseen domain from strokes.

Diffusion probabilistic models may include a type of latent variable model that consist of a forward diffusion process and a reverse diffusion process. The forward process is a Markov chain where noise is gradually added to the data when sequentially sampling the latent variables $x_t$ for $t=1, \ldots, T$. Each step in the forward process is a Gaussian transition (e.g., $q(x_t|x_{t-1}) := N(\sqrt{1-\beta_t}x_{t-1}), \beta_t, I)$, where $\beta_t|_{t=0}^T$ are fixed or learned variance schedule. The resulting latent variable $x_t$ can be expressed as:

$$x_t = \sqrt{\alpha_t}x_0 + \sqrt{1-\alpha_t}w_t, w_t \sim N(0,1)$$

Where $\alpha_t = \Pi s = 1t(1-\beta s)$. The reverse process xt−1|xt is parametrized by another Gaussian transition $p\theta(xt-1|xt) = N(xt-1; \mu\theta(xt,t), \Sigma\theta(xt,t))$, $\mu\theta(xt,t)$ can be decombed into the linear combination $x_t$ and a noise approximation model $\epsilon\theta(xt, t)$ which can be learned by solving the optimization problem as follows:

$$\min_\theta E_{x_0 \sim q(x_0), w \sim N(0,1), t} \|w - \epsilon\theta(x_t, t)\|_2^2$$

After training $\epsilon\theta(xt, t)$, the data is sampled using following reverse diffusion process:

$$x_{t-1} = \frac{1}{\sqrt{1-\beta_t}}\left(x_t - \frac{1-\alpha_t}{\sqrt{1-\bar{\alpha}_t}}\epsilon_\theta(x_t, t)\right) + \sigma_t z, z \sim \mathcal{N}(0, I)$$

Where $z \sim N(0,I)$. It was found that the sampling process of DDPM corresponds to that of the score-based generative models with the following relationship:

$$\epsilon_\theta(x_t, t) = -\sqrt{1-\bar{\alpha}_t}\nabla_{x_t} \log p_\theta(x_t).$$

Meanwhile, an alternative non-Markovian nosing process that has the same forward marginals as DDPM but has a distinct sampling process as follows:

$$x_{t-1} = \sqrt{\bar{\alpha}_{t-1}}f_\theta(x_t,t) + \sqrt{1-\alpha_{t-1}-\sigma_t^2}\epsilon_\theta(x_t,t) + \sigma_t^2 z,$$

Where, $z \sim N(0,I)$ and $f\theta(xt,t)$ is the prediction of $x_0$ at given $x_t$ and $t$ and $\epsilon_\theta(x_t, t)$:

$$f_\theta(x_t, t) := \frac{x_t - \sqrt{1-\alpha_t}\epsilon_\theta(x_t, t)}{\sqrt{\bar{\alpha}_t}}.$$

CLIP was proposed to efficiently learn visual concepts with natural language supervision. In CLIP, a text encoder and an image encoder are pretrained to identify which texts are matched with which images in the dataset. Accordingly, we use a pretrained CLIP model for text-driven image manipulation.

To effectively extract knowledge from CLIP, two different losses have been proposed: a global target loss, and a local directional loss. The global CLIP loss tries to minimize the cosine distance in the CLIP space between the generated image and a given target text as follows:

$$L_{global}(x_{gen}, y_{tar}) = D_{CLIP}(x_{gen}, y_{tar})$$

Where $y_{tar}$ is a text description of a target, $x_{gen}$ denotes the generated image, and $D_{CLIP}$ returns a cosine distance in the CLIP space between their encoded vectors. On the other hand, the local directional loss is designed to alleviate issues of global CLIP loss such as low diversity and susceptibility to adversarial attacks. The local directional CLIP loss induces the direction between the embeddings of the reference and generated images to be aligned with the direction between the embeddings of a pair of reference and target texts in the CLIP space as follows:

$$L_{(direction)}(x_{gen}, y_{tar}; x_{ref}, y_{ref}) := 1 - \frac{\Delta I, \Delta T}{\|\Delta I\|\|\Delta T\|},$$

where $$\Delta T = ET(y_{tar}) - ET(y_{ref}), \Delta I = EI(x_{gen}) - EI(x_{ref})$$

Here, $E_I$ and $E_T$ are CLIP's image and text encoders, respectively, and $y_{ref}, x_{ref}$ are the source domain text and image, respectively. The manipulated images guided by the directional CLIP loss are known to be robust to mode-collapse issues because by aligning the direction between the image representations with the direction between the reference text and the target text, distinct images should be generated. Furthermore, this method is more robust to adversarial attacks because the perturbation will differ depending on the images.

Continuing to refer to FIG. 8, in terms of fine-tuning, the latent or diffusional model may be modified itself. The following equation may be used to identifying the directional CLIP loss and the identity loss:

$$L_{direction}(\hat{x}_0(\theta), y_{tar}; x_0, y_{ref}) + L_{id}(\hat{x}_0(\theta), x_0)$$

In the given context, $x_0$ represented the original image, while $\hat{x}_0(\theta)$ is the generated image obtained from the latent $x_{t0}$ using the optimized parameter $\hat{\theta}$. Moreover, $y_{ref}$ is the reference text and $y_{tar}$ is the target text that has been provided for the purpose of image manipulation.

In this approach, the CLIP loss functions as the primary supervisory signal for the optimization process. Among the two types of CLIP losses discussed earlier, the directional CLIP loss is utilized for its beneficial characteristics. The implementation of directional CLIP loss during training necessitates a reference text $y_{ref}$ and a target text $y_{tar}$.

Continuing to refer to FIG. 8, at process 812, the backward model may be fed with the latent representation to generate a final output by generating an intermediate ECHO image iteratively under the guidance of the CLIP model. The final output may normally be obtainable by analyzing an ECHO image. In some embodiments, the output may be a 2-D image, a 3-D image of an ECHO. The generative model may take the representation of the target ECG signal as a conditioning input, and visualize the information (e.g., potential disease conditions) hidden in the target ECG signal on the representation of the base ECHO image (e.g., an ECHO images for a healthy people), thus deriving a new ECHO image. As those skilled in the art will appreciate, the reverse process is parametrized by another Gaussian transition (e.g., the backward model) where the latent representation is iteratively denoised by generating an intermediate outcome (e.g., an intermediate ECHO image) iteratively.

Continuing to refer to FIG. 8, the CLIP model may guide the generation of the intermediate ECHO image at each iteration towards the target ECG signal. Since the CLIP may predict the closest ECHO image based on the input ECG signal, or vice versa, the CLIP model may guide the generation by comparing the similarity between the intermediate ECHO image and the target ECG signal. For example, the CLIP loss function of the CLIP model may compute the gradient of target ECG signal and the intermediate ECHO image similarity, with respect to the intermediate ECHO image. In some embodiments, the additional loss function of the CLIP model computes the loss by taking some or all the following values as input(s): the intermediate ECHO image generated at each iteration, the target ECG signal, the base ECHO image, and the base ECG signal. For example, the CLIP model computes a global target loss, e.g., by taking as input the intermediate ECHO image and the target ECG signal. As the other example, the CLIP model computes the local directional loss, e.g., by taking as input the intermediate ECHO image, the target ECG signal, the base ECHO image, and the base ECG signal.

Figure 9A:
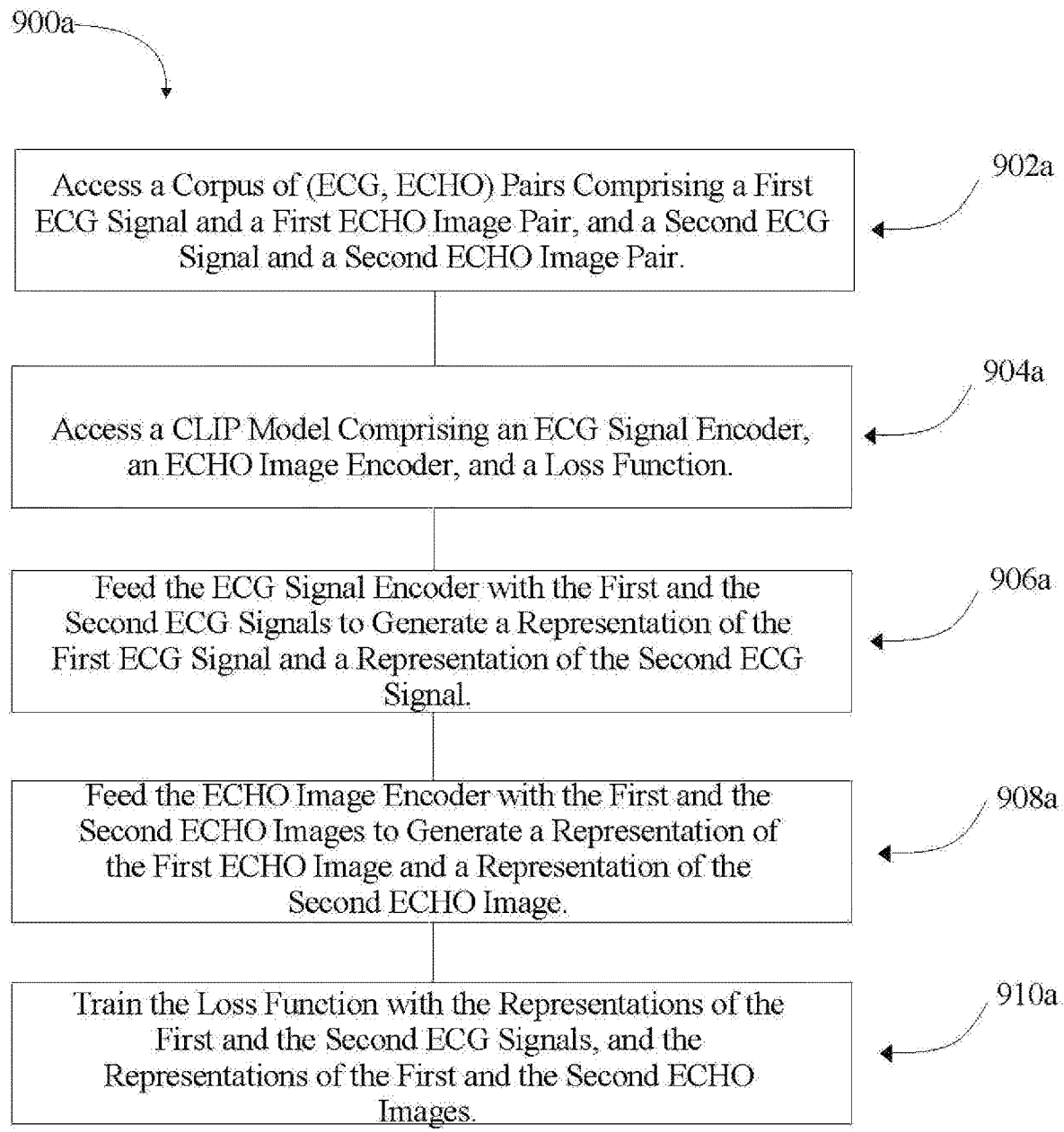
FIG. 9A is a diagrammatic representation of a method for training a CLIP model, in accordance with certain embodiments of the present disclosure.

FIG. 9A illustrates a simplified diagram of a method 900a for training a CLIP model in accordance with certain embodiments of the present disclosure. According to some embodiments consistent with FIG. 9A, method 900a may be performed by a computer processor, such as processor 112 based on instructions and/or data stored in a memory, such as memory 116. The trained CLIP model may take an ECG as the input to generate the closest ECHO, vice versa. The trained CLIP model may also take an (ECG, ECHO) pair as the input to generate a similarity score of the (ECG, ECHO) pair.

Continuing to refer to FIG. 9A, at process 902a, a corpus of (ECG, ECHO) pairs may be accessed. The corpus of ECG signal and ECHO image pairs may include a first ECG signal and a first ECHO image pair, and a second ECG signal and a second ECHO image pair. In some embodiments, the ECG signal may be a continuous or discrete representation of an ECG signal generated by some or all the models as described above. The ECHO image may be a continuous or discrete representation of an ECHO image generated by some or all the models as described above. In some embodiments, the corpus of ECG signal and ECHO image pairs may be accessed by the database, such as database 104. In some embodiments, additional processes need to be performed to access the ECG signal, as described with reference to FIG. 3.

Continuing to refer to FIG. 9A, at process 904a, a CLIP model, such as the CLIP model 152, may be accessed. The CLIP model may include an ECG signal encoder, an ECHO image encoder, and a loss function. In some embodiments, the CLIP model may be a CyCLIP model.

Continuing to refer to FIG. 9A, at process 906a, the ECG signal encoder may be fed with the first and the second ECG signals to generate a representation of the first ECG signal (e.g., an embedding) and a representation of the second ECG signal.

Continuing to refer to FIG. 9A, at process 908a, the ECHO image encoder may be fed with the first and the second ECHO images to generate a representation of the first ECHO image (e.g., an embedding) and a representation of the second ECHO image.

Continuing to refer to FIG. 9A, at process 910a, the loss function may be trained by the representation of the first ECG signal, the representation of the second ECG signal, the representation of the first ECHO image and the representation of the second ECHO image. Specifically, the loss function may be trained by performing some or all the following sub-steps: (a) reducing a distance (e.g., cosine distance) between the representations of the first ECG signal and the first ECHO image, (b) reducing a distance between the representations of the second ECG signal and the second ECHO image, (c) increasing a distance between the representations of the first ECG signal and the second ECHO image, and (d) increasing a distance between the representation of the second ECG signal and the first ECHO image. In some embodiments, extra steps such as symmetrizing cross-modal consistency and/or in-modal consistency may be performed to further optimize the performance of CLIP model. Specifically, the loss function may be further trained by performing some or all the following steps: (a) ensuring the distance in sub-steps (a) above is roughly the same as the distance in sub-steps (b) above, and (b) ensuring a distance between the representations of the first and the second ECG signals is roughly the same as a distance between the representation of the first and the second ECHO images.

Figure 9B:
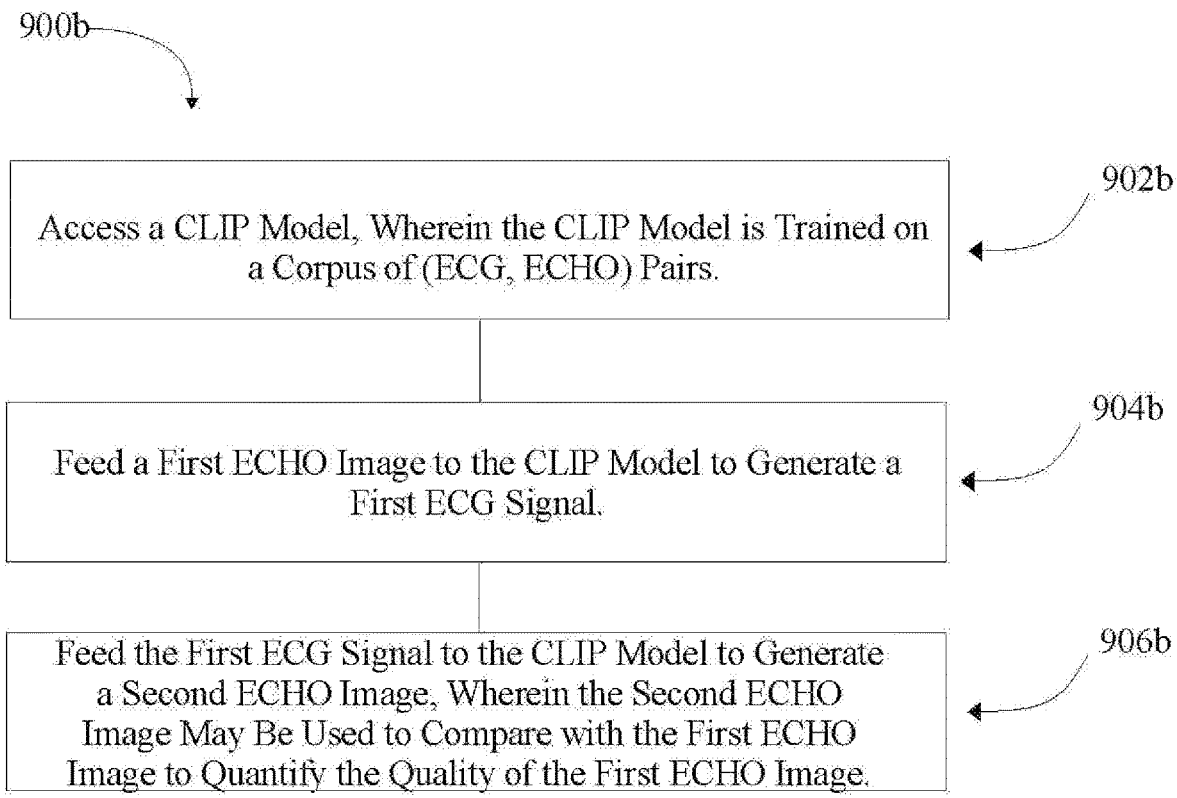
FIG. 9B is a diagrammatic representation of a method for using a trained CLIP model to quantify the quality of an ECHO image, in accordance with certain embodiments of the present disclosure.

FIG. 9B illustrates a simplified diagram of a method 900b for using a trained CLIP model to quantify the quality of an ECHO image, such as the CLIP model 152, in accordance with certain embodiments of the present disclosure. According to some embodiments consistent with FIG. 9B, method 900b may be performed by a computer processor, such as processor 160 based on instructions and/or data stored in a memory, such as memory 150.

Continuing to refer to FIG. 9B, at process 902b, a CLIP model may be accessed. The CLIP model may be trained on a corpus of (ECG, ECHO) pairs. The model may be trained by performing some or all the process in FIG. 9A. As discussed above, at the inference stage, the trained CLIP model may take an image as an input and output the corresponding label (often with the prompt), and vice versa. For example, the trained CLIP model may take a specific ECG signal as an input and generate the closest matching ECHO image. Similarly, the trained CLIP model may take a specific ECHO image as an input and generate the closest matching ECG signal. In some embodiments, the CLIP model maybe a CyCLIP model Continuing to refer to FIG. 9B, at process 904b, a first ECHO image may be fed to the trained CLIP model to generate a first ECG signal. The first ECHO image may be a continuous or discrete representation of any ECHO image generated by some or all the models as described above. In some embodiments, the first ECHO image may be the intermediate ECHO image and/or the final ECHO image generated in FIG. 8 above.

Continuing to refer to FIG. 9B, at process 906b, the first ECG signal may be fed to the trained CLIP model to generate a second ECHO image. The second ECHO image may be used to compare with the first ECHO image to quantify the quality of the first ECHO image. Some or all the process may be repeated to quantify the quality of an ECG signal. For example, a first ECG signal may be fed to the trained CLIP model to generate a first ECHO image. The first ECHO image may be fed to the trained CLIP model to generate a second ECG signal. The second ECG signal may be used to compare with the first ECG signal to quantify the quality of the first ECG signal.

Figure 10:
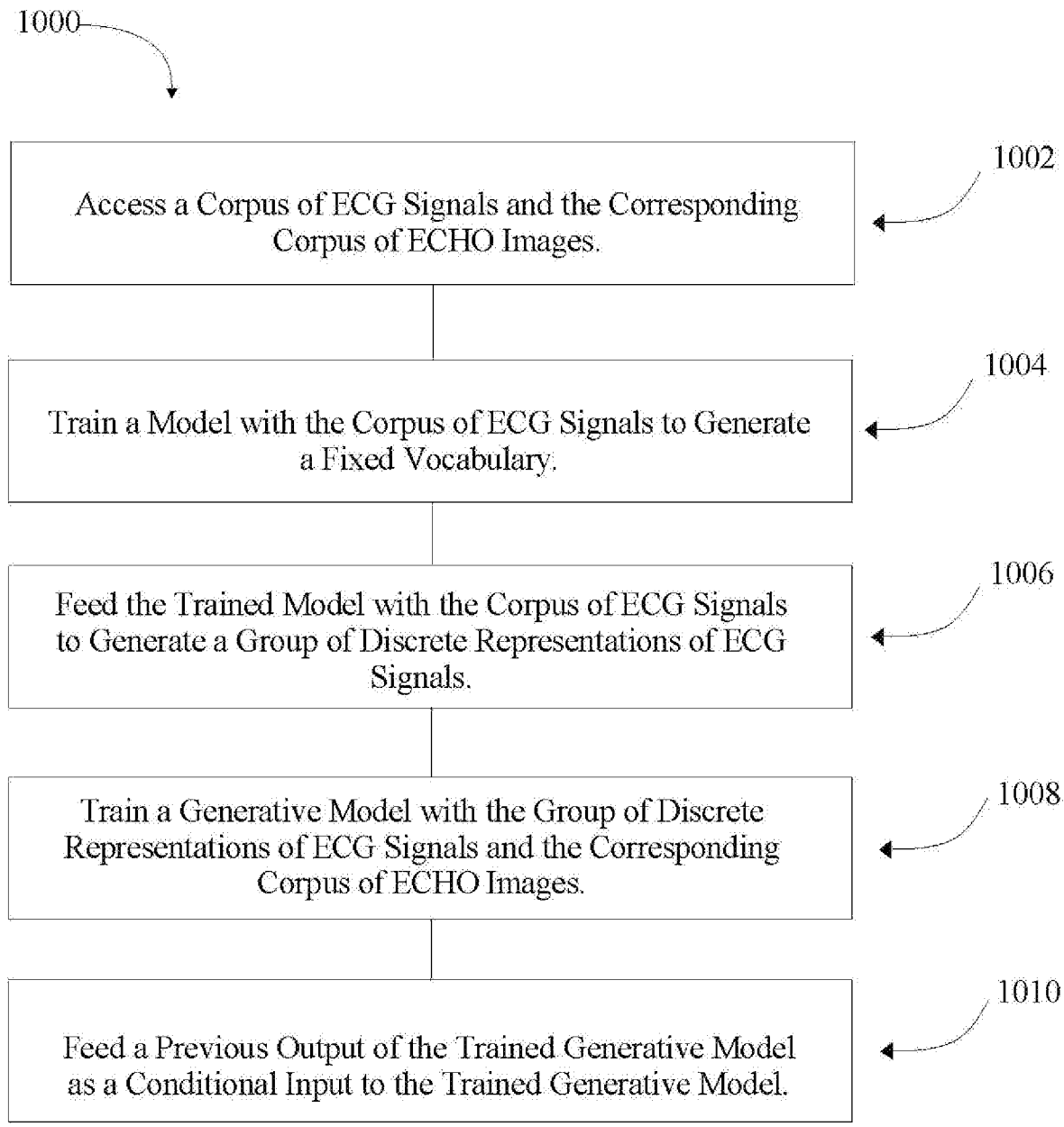
FIG. 10 is a diagrammatic representation of a method for generating an output based on an ECG, in accordance with certain embodiments of the present disclosure.

FIG. 10 illustrates a simplified diagram of a method 1000 for generating an output based on an ECG, such as the ECG device 104, in accordance with certain embodiments of the present disclosure. According to some embodiments consistent with FIG. 10, method 1000 may be performed by a computer processor, such as processor 112 based on instructions and/or data stored in a memory, such as memory 116. The trained diffusion model may take an ECG signal as input to generate the 2D/3D ECHO and/or a sequence of 2D/3D ECHO which may be used for disease diagnosis.

Continuing to refer to FIG. 10, at process 1002, a corpus of ECG signals and the corresponding corpus of ECHO images may be accessed. Each ECG signal among the corpus of the ECG signals may have a corresponding ECHO image(s) among the corpus of ECHO images. For example, a first ECG signal has a corresponding first ECHO image, or a first sequence of ECHO images. The process 1002 may be similar to some or all the processes described, e.g., the process 202a.

Continuing to refer to FIG. 10, at a process 1004, a model may be trained with the corpus of ECG signals to generate a fixed vocabulary. The fixed vocabulary can represent any ECG signal as a discrete representation of that ECG signal. In some embodiments, the parameters of the model are updated using backpropagation over each iteration. The process 1004 may be similar to some or all the processes described, e.g., the process 204a.

Continuing to refer to FIG. 10, at process 1006, the trained model may be fed with the corpus of ECG signal to generate a group of discrete representations of ECG signals. In some embodiments, the first ECG signal may be transformed into a representation of the first ECG signal. The process 1006 may be similar to some or all the processes described, e.g., the process 206a.

Continuing to refer to FIG. 10, at process 1008, a generative model, such as a diffusion model, may be trained with the group of discrete representations of ECG signals and the corresponding corpus of ECHO images. For example, the representation of the first ECG signal and its corresponding first ECHO image may be used to train the generative model. In some embodiments, the generative model may be trained in supervised learning manner. For example, the group of discrete representations of ECG signals may be used as conditioning input to train the generative model, and the corresponding corpus of ECHO images may be used as input to train the generative model. The generative model may be trained to output a 2D/3D ECHO image. The doctors may use such the image for diagnosis. The process 1008 may be similar to some or all the processes described, e.g., the process 606.

Continuing to refer to FIG. 10, at a process 1010, a previous output of the trained generative model may be provided as a conditional input to the generative model. In some embodiments, the previous output may be the output generating in the processor 1008. The previous output and the new output are capable of forming an image sequence (e.g., a proxy for a video) of ECHO images. In some embodiments, the image sequence can depict the development of disease condition continuously. The process 1010 may be similar to some or all the processes described, e.g., the process 712.

Figure 11:
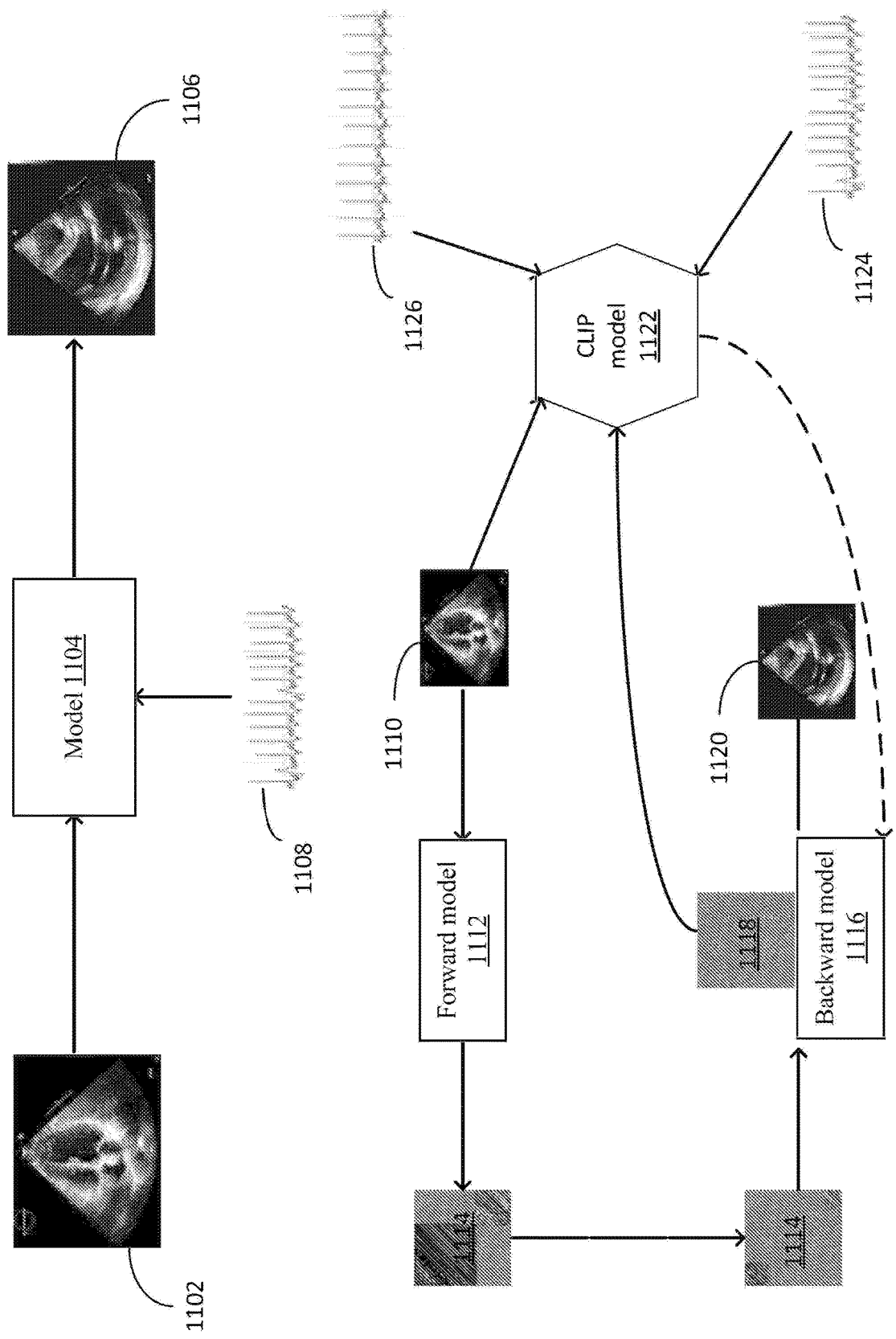
FIG. 11 is a diagrammatic representation of fine-tuning a diffusion model to manipulate the output based on ECG signal, in accordance with certain embodiments of the present disclosure.

FIG. 11, illustrates a schematic diagram of fine-tuning a diffusion model to manipulate the output based on ECG signal, in accordance with certain embodiments of the present disclosure, Accordingly, to some embodiments consistent with FIG. 11, the diffusion model may be the generative model described in FIG. 8. The base of ECHO image 1102 is transformed by a generative model, such as the diffusional model into the final ECHO image 1106. The final ECHO image is manipulated by the target ECG signal 1108. The generative model may take the target ECG signal 1108 as a conditioning input, and visualize the information (e.g., potential disease conditions) hidden in the target ECG signal 1108 on the base ECHO image 1102 (e.g., an ECHO image for a health people), thus deriving a new ECHO image 1106. Specifically, a base ECHO image 1110, a corresponding base ECG signal 1126 and the target ECG signal 1124 are accessed. In some embodiments, the base ECHO image 1110 and the base ECG signal 1126 doesn't reflect any disease condition (e.g., normal, healthy). The target ECG signal 1124 may reflect disease condition (e.g., CHD). The base ECHO image 1110 and the corresponding base ECG signal 1126 on the one hand, and the target ECG signal 1124 on the other, may come from the same or different people. For example, the base ECHO image 1110 and the based ECG signal 1126 may come from a healthy people A The target ECHO signal 1124 may come from a patient B, or from the people A when s/he ills. During the forward diffusion process, a forward model 1112 of the diffusion model 1104 is fed with the base ECHO image 1110 to generate a latent representation of the base ECHO image 1114 (e.g., noise distribution). During the backward diffusion process, the forward model 1112 will be copied to a backward model 1116 of the diffusion model 1104, and the backward model 1116 is def with the latent representation 1114 to generate a final output by generating an intermediate ECHO image 1118 iteratively under the guidance of the CLIP model 1122. The CLIP model 1122 guides the generation of the intermediate ECHO image at each iteration towards the target ECG signal. Specifically, the loss function of the CLIP model 1122 computes the loss by taking some or all the following values as input(s): the base ECHO image 1110, the base ECG signal 1126, the intermediate image 1118 generated during each iteration, and the target ECG signal 1124.

Continuing to refer to FIG. 11, the subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

Continuing to refer to FIG. 11, the processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

Continuing to refer to FIG. 11, to provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

Continuing to refer to FIG. 11, the subject matter described herein can be implemented in a computing system that includes a back-end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Continuing to refer to FIG. 11, techniques for generating echocardiogram information from an electrocardiogram have been disclosed. The summary below provides a non-limiting and non-exhaustive overview of certain embodiments of the disclosed techniques. Further details of these embodiments may be found throughout the disclosure above.

Figure 12:
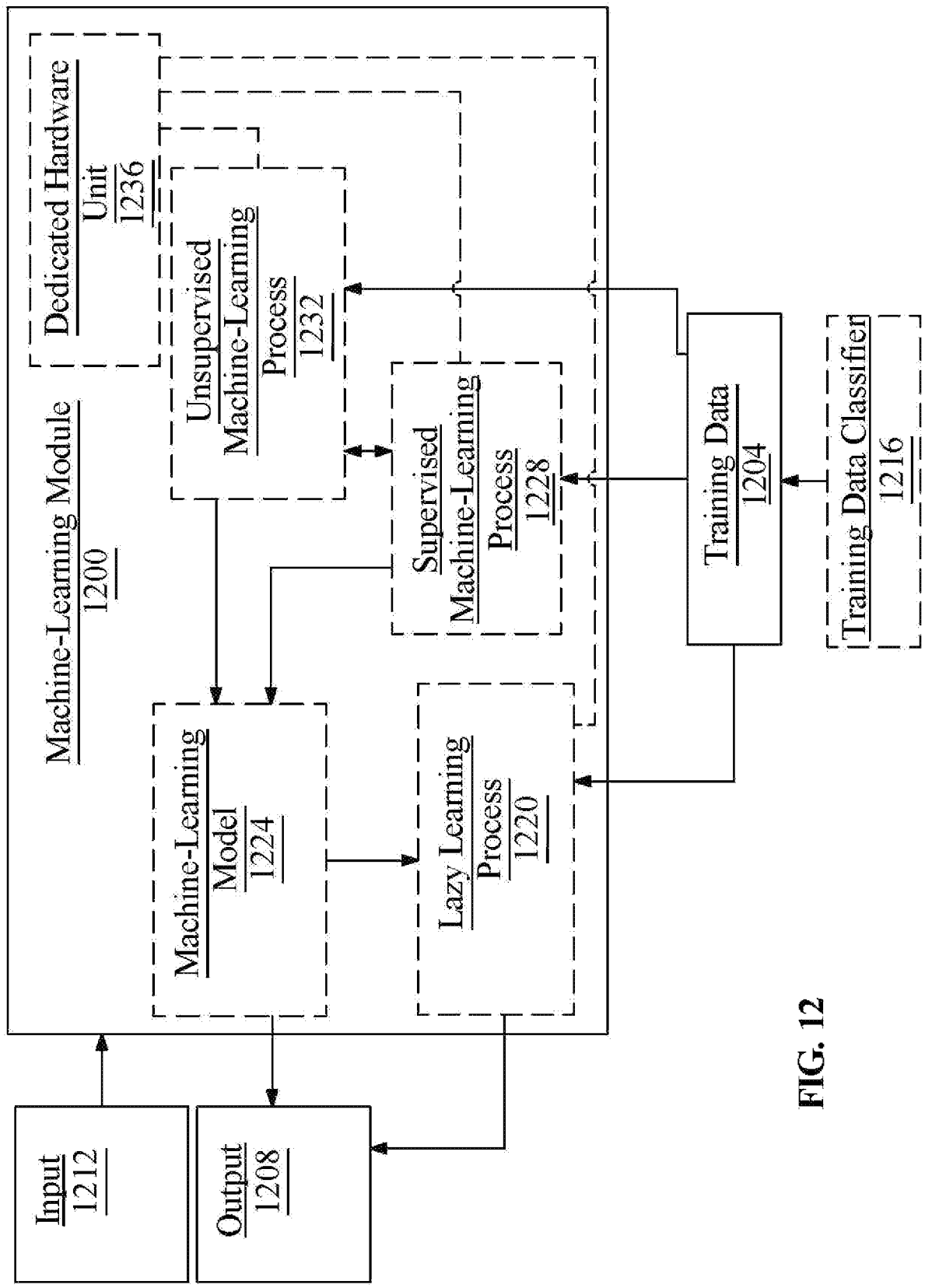
FIG. 12 is a block diagram of an exemplary machine-learning process.

Referring now to FIG. 12, an exemplary embodiment of a machine-learning module 1200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 1204 to generate an algorithm instantiated in hardware or software logic, data structures, and/or functions that will be performed by a computing device/module to produce outputs 1208 given data provided as inputs 1212; this is in contrast to a non-machine learning software program where the commands to be executed are determined in advance by a user and written in a programming language.

Still referring to FIG. 12, "training data," as used herein, is data containing correlations that a machine-learning process may use to model relationships between two or more categories of data elements. For instance, and without limitation, training data 1204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 1204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1204 according to various correlations; correlations may indicate causative and/or predictive links between categories of data elements, which may be modeled as relationships such as mathematical relationships by machine-learning processes as described in further detail below. Training data 1204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 1204 may be linked to descriptors of categories by tags, tokens, or other data elements; for instance, and without limitation, training data 1204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 12, training data 1204 may include one or more elements that are not categorized; that is, training data 1204 may not be formatted or contain descriptors for some elements of data. Machine-learning algorithms and/or other processes may sort training data 1204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1204 to be made applicable for two or more distinct machine-learning algorithms as described in further detail below. Training data 1204 used by machine-learning module 1200 may correlate any input data as described in this disclosure to any output data as described in this disclosure.

Further referring to FIG. 12, training data may be filtered, sorted, and/or selected using one or more supervised and/or unsupervised machine-learning processes and/or models as described in further detail below; such models may include without limitation a training data classifier 216. Training data classifier 1216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 1200 may generate a classifier using a classification algorithm, defined as a processes whereby a computing device and/or any module and/or component operating thereon derives a classifier from training data 1204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With further reference to FIG. 12, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 12, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 12, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 12, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 12, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 12, machine-learning module 1200 may be configured to perform a lazy-learning process 1220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1204. Heuristic may include selecting some number of highest-ranking associations and/or training data 1204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 12, machine-learning processes as described in this disclosure may be used to generate machine-learning models 1224. A "machine-learning model," as used in this disclosure, is a data structure representing and/or instantiating a mathematical and/or algorithmic representation of a relationship between inputs and outputs, as generated using any machine-learning process including without limitation any process as described above and stored in memory; an input is submitted to a machine-learning model 1224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 12, machine-learning algorithms may include at least a supervised machine-learning process 1228. At least a supervised machine-learning process 1228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include a plurality of ECG images as described above as inputs, an aggregate ECG data repository as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1204. Persons skilled in the art, upon reviewing the entirety of this disclosure, will be aware of various possible variations of at least a supervised machine-learning process 1228 that may be used to determine relation between inputs and outputs. Supervised machine-learning processes may include classification algorithms as defined above.

With further reference to FIG. 12, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 12, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 12, machine learning processes may include at least an unsupervised machine-learning processes 1232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 1232 may not require a response variable; unsupervised processes 1232 may be used to find interesting patterns and/or inferences between variables, to determine a degree of correlation between two or more variables, or the like.

Still referring to FIG. 12, machine-learning module 1200 may be designed and configured to create a machine-learning model 1224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 12, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 12, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 12, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 12, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 12, one or more processes or algorithms described above may be performed by at least a dedicated hardware unit 1236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 1236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 1236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 1236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 13:
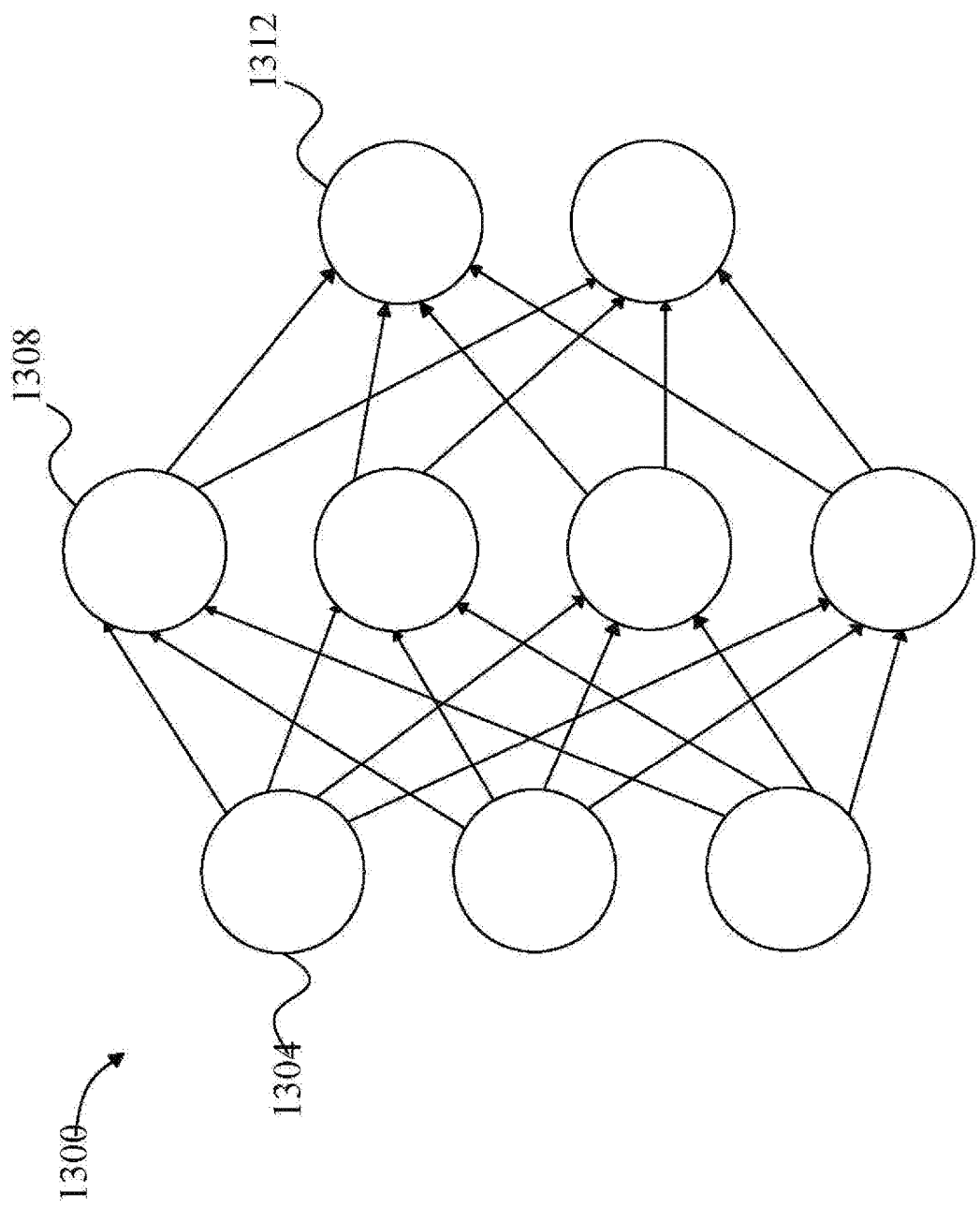
FIG. 13 is a diagram of an exemplary embodiment of a neural network.

Referring now to FIG. 13, an exemplary embodiment of neural network 1300 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 1304, one or more intermediate layers 1308, and an output layer of nodes 1312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 14:
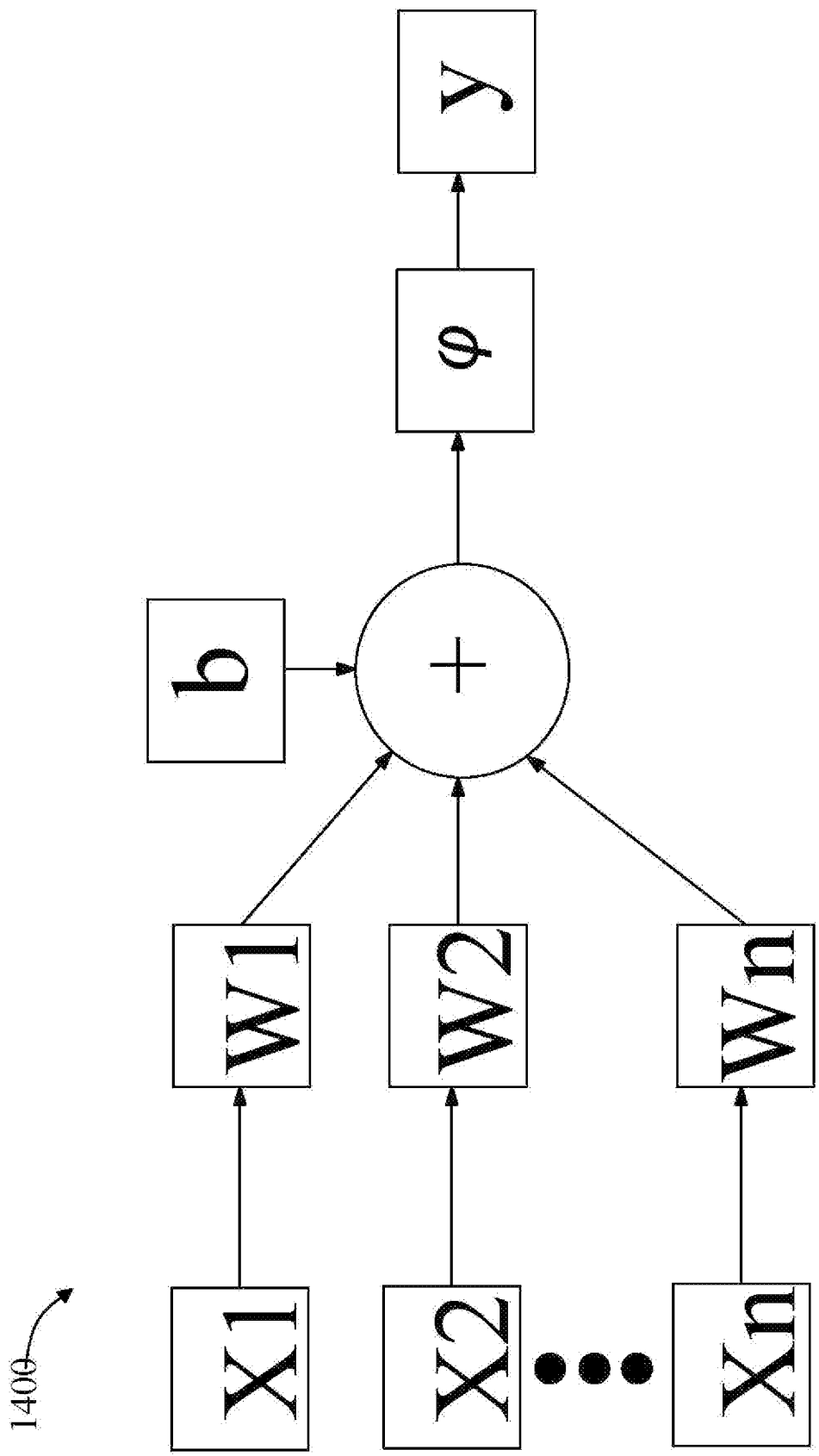
FIG. 14 is a diagram of an exemplary embodiment of a node of a neural network.

Referring now to FIG. 14, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 15:
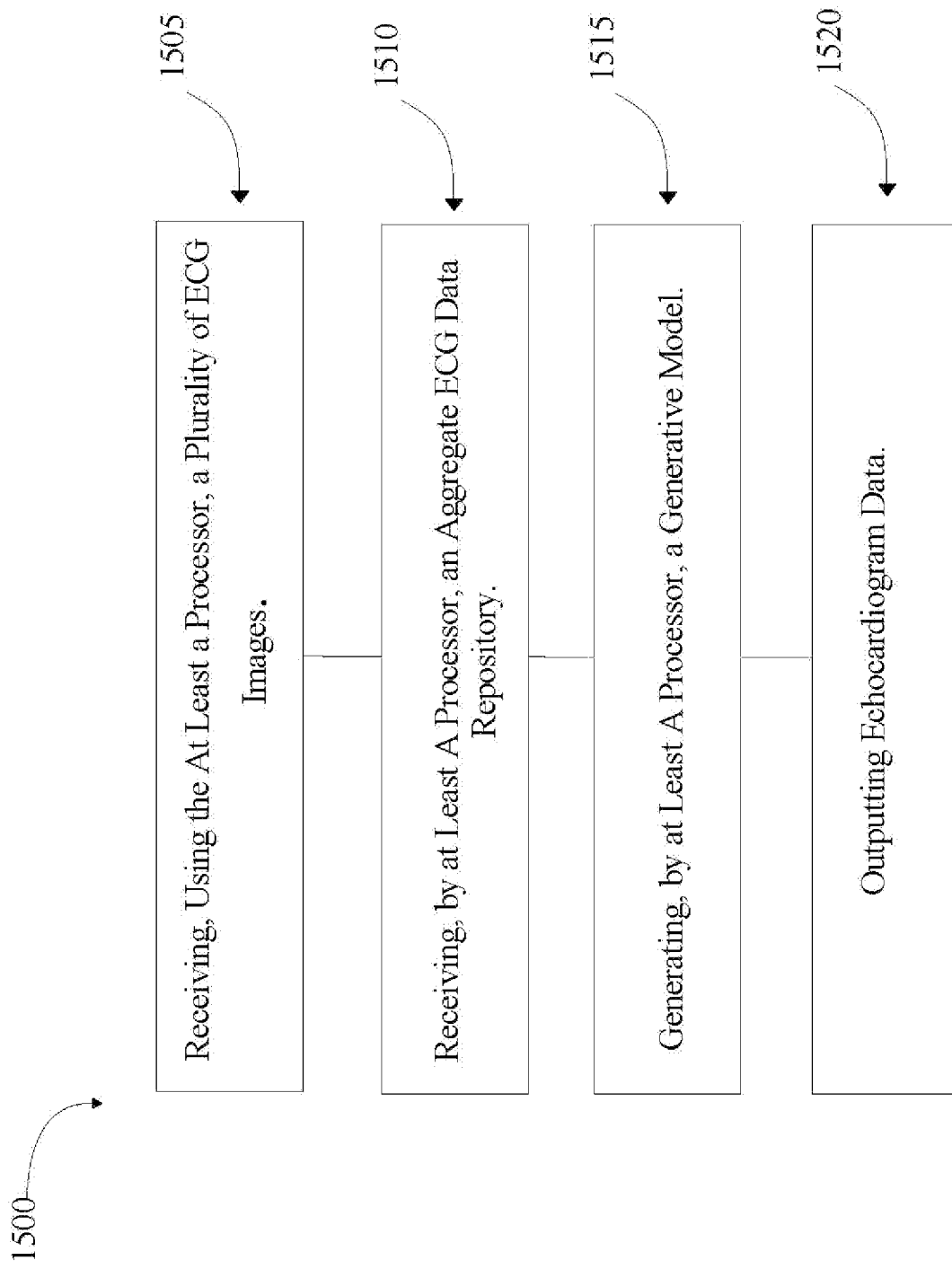
FIG. 15 is a flow diagram of an exemplary method of generating imaging information based on at least a signal.

Referring now to FIG. 15, a flow diagram of an exemplary method 1500 for generating imaging information based on at least a signal is illustrated. At step 1505, method 1500 includes receiving, using the at least a processor, a plurality of ECG images. This may be implemented with reference to FIGS. 1-14.

Still referring to FIG. 15, at step 1510, method 1500 includes receiving, by the at least a processor, an aggregate ECG data repository. This may be implemented with reference to FIGS. 1-14.

Still referring to FIG. 15, at step 1515, method 1500 includes generating, by the at least a processor, a generative model wherein generating the generative model comprises training the generative model using generative training data. This may be implemented with reference to FIGS. 1-14. In an embodiment, the generative model is a machine learning model. In another embodiment, the generative model is a neural network. In another embodiment, generative training data comprises at least a plurality of ECG images as input. In another embodiment, generative training data comprises at least an aggregate ECG data repository as input.

Still referring to FIG. 15, at step 1520, method 1500 includes outputting echocardiogram data as a function of the trained generative model. This may be implemented with reference to FIGS. 1-14.

Figure 16:
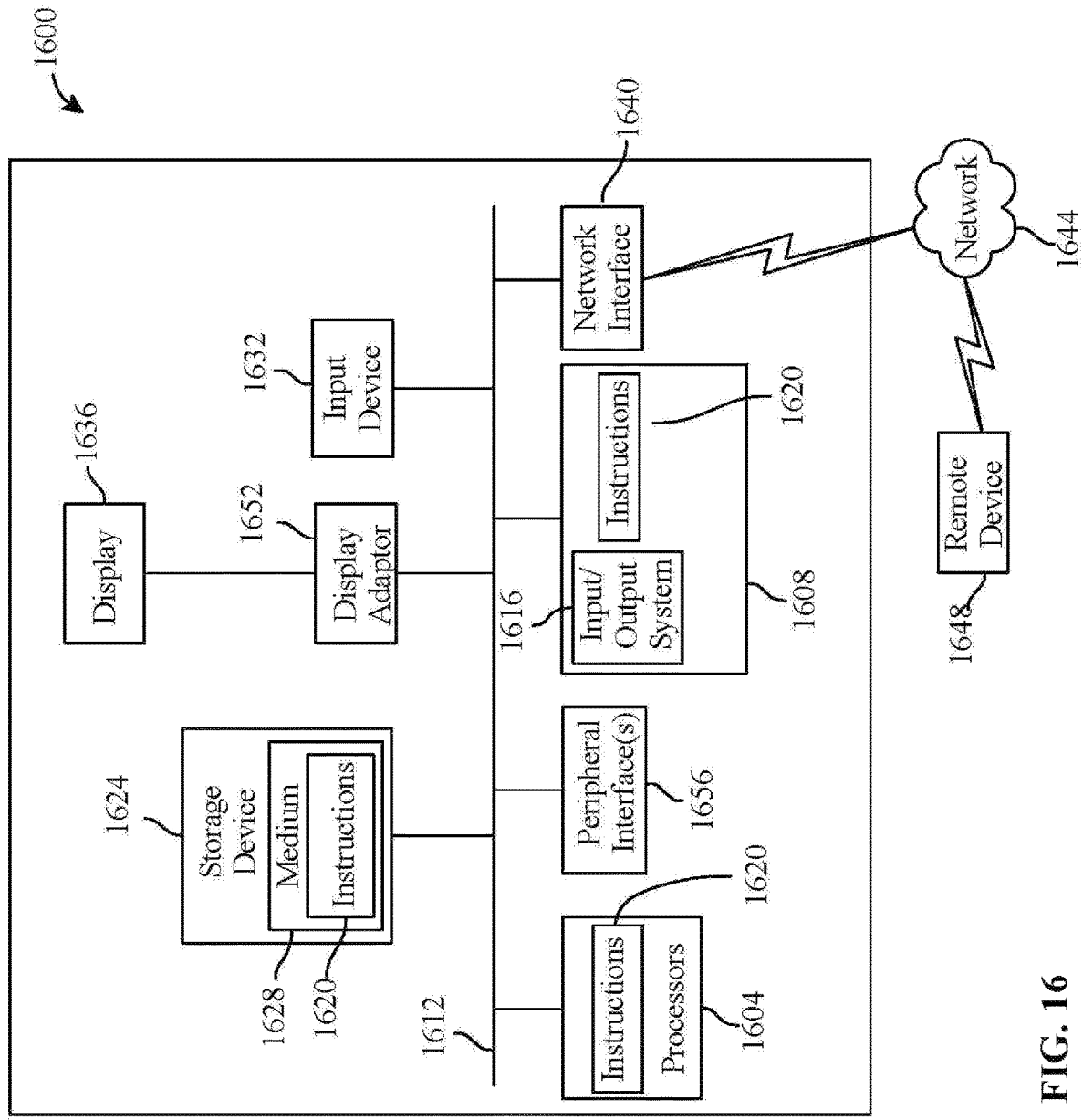
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Processor 1604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1604 may be organized according to Von Neumann and/or Harvard architecture as a non-limiting example. Processor 1604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1608 may include various components (e.g., machine-readable media) including, but not limited to, a random-access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIREWIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636. Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating imaging information based on at least a signal comprising:
   at least a processor; and
   a non-transitory computer executable storage medium communicatively connected to the at least a processor, wherein the non-transitory computer executable storage medium containing instructions configuring the at least a processor to:
   receive a plurality of ECG images;
   receive an aggregate ECG data repository, wherein the aggregate ECG data repository correlates ECG data with simulated echocardiogram data;
   generate a generative model as a function of the plurality of ECG images and the ECG data repository wherein generating the generative model comprises:
   training the generative model using generative training data, wherein the generative training data correlates at least an ECG signal from a corpus of ECG signals and includes user feedback, wherein the user feedback indicates whether output of the generative model should be used or removed from the generative training data;
   calculate an accuracy score as a function of the user feedback;
   update the generative training data as a function of the accuracy score; and
   iteratively train the generative model as a function of the updated generative training data;
   output, at a viewer, simulated echocardiogram data as a function of the trained generative model.

2. The system of claim 1, wherein the generative model is a machine learning model.

3. The system of claim 1, wherein the generative model is a neural network.

4. The system of claim 1, wherein the generative model is an autoregressive model.

5. The system of claim 1, wherein generative training data comprises at least a plurality of ECG images input.

6. The system of claim 1, wherein the generative training data comprises at least a corpus of ECG related data input.

7. The system of claim 1, wherein generating the generative model comprises generating a quantizing model wherein the quantizing model is configured to compress the aggregate ECG data repository.

8. The system of claim 1, wherein generating the generative model further comprises generating an autoregressive model, wherein the autoregressive model is configured to transform the aggregate ECG data repository into at least a sequence of numeric tokens.

9. The system of claim 1, wherein generating the generative model comprises:
   producing a processing output using the plurality of ECG images and at least a processing model; and
   generating the generative model using the processing output.

10. The system of claim 1, wherein generating the generative model comprises generating a contrastive learning model, wherein the contrastive learning model is configured to contrast at least a plurality of ECG images against each other.

11. A method for generating imaging information based on at least a signal comprising:
    receiving, by at least a processor, a plurality of ECG images;
    receiving, by the at least a processor, an aggregate ECG data repository, wherein the aggregate ECG data repository correlates ECG data with simulated echocardiogram data;
    generating, by the at least a processor, generative model as a function of the plurality of ECG images and the ECG data repository wherein generating the generative model comprises:
    training the generative model using generative training data, wherein the generative training data correlates at least an ECG signal from a corpus of ECG signals and includes user feedback, wherein the user feedback indicates whether output of the generative model should be used or removed from the generative training data;
    calculate an accuracy score as a function of the user feedback;
    update the generative training data as a function of the accuracy score; and
    iteratively train the generative model as a function of the updated generative training data;
    output, at a viewer, simulated echocardiogram data as a function of the trained generative model.

12. The method of claim 11, wherein the generative model is a machine learning model.

13. The method of claim 11, wherein the generative model is a neural network.

14. The method of claim 11, wherein the generative model is an autoregressive model.

15. The method of claim 11, wherein generative training data comprises at least a plurality of ECG images input.

16. The method of claim 11, wherein the generative training data comprises at least an aggregate ECG data repository input.

17. The method of claim 11, wherein generating the generative model comprises generating a quantizing model wherein the quantizing model is configured to compress the aggregate ECG data repository.

18. The method of claim 11, wherein generating the generative model further comprises generating an autoregressive model, wherein the autoregressive model is configured to transform the aggregate ECG data repository into at least a sequence of numeric tokens.

19. The method of claim 11, wherein generating the generative model comprises:
   producing a processing output using the plurality of ECG images and at least a processing model; and
   generating the generative model using the processing output.

20. The method of claim 11, wherein generating the generative model comprises generative a contrastive learning model, wherein the contrastive learning model is configured to contrast at least a plurality of ECG images against each other.

* * * * *